(12) United States Patent
Atreja et al.

(10) Patent No.: US 11,791,020 B2
(45) Date of Patent: Oct. 17, 2023

(54) SYSTEMS AND METHODS FOR MONITORING SUBJECTS HAVING CHRONIC GASTROINTESTINAL INDICATIONS

(71) Applicant: Icahn School of Medicine at Mount Sinai, New York, NY (US)

(72) Inventors: Ashish Atreja, New York, NY (US); Jason Rogers, New York, NY (US); Milan Patel, New York, NY (US)

(73) Assignee: ICAHN SCHOOL OF MEDICINE AT MOUNT SINAI, New York, NY (US)

( * ) Notice: Subject to any disclaimer, the term of this patent is extended or adjusted under 35 U.S.C. 154(b) by 287 days.

(21) Appl. No.: 15/999,470

(22) PCT Filed: Feb. 17, 2017

(86) PCT No.: PCT/US2017/018503
§ 371 (c)(1),
(2) Date: Aug. 17, 2018

(87) PCT Pub. No.: WO2017/143284
PCT Pub. Date: Aug. 24, 2017

(65) Prior Publication Data
US 2020/0381086 A1 Dec. 3, 2020

Related U.S. Application Data

(60) Provisional application No. 62/297,720, filed on Feb. 19, 2016.

(51) Int. Cl.
*G16H 10/20* (2018.01)
*G16H 15/00* (2018.01)
(Continued)

(52) U.S. Cl.
CPC ........... *G16H 10/20* (2018.01); *A61B 5/0022* (2013.01); *A61B 5/1118* (2013.01); *A61B 5/411* (2013.01);
(Continued)

(58) Field of Classification Search
CPC ........ G16H 10/20; G16H 40/67; G16H 40/20; G16H 50/50; G16H 15/00; G16H 20/10;
(Continued)

(56) References Cited

U.S. PATENT DOCUMENTS

2004/0122706 A1* 6/2004 Walker ................... G16H 50/20
706/45
2007/0258894 A1* 11/2007 Melker ................ G01N 33/497
424/9.1

(Continued)

FOREIGN PATENT DOCUMENTS

KR 10-2013-0140589 A 12/2013

OTHER PUBLICATIONS

A. Honka et al., "Rethinking Health: ICT-Enabled Services to Empower People to Manage Their Health," in IEEE Reviews in Biomedical Engineering, vol. 4, pp. 119-139, 2011, doi: 10.1109/RBME.2011.2174217. (Year: 2011).*

(Continued)

*Primary Examiner* — Christopher L Gilligan
*Assistant Examiner* — Bennett Stephen Erickson

(57) ABSTRACT

Systems and methods are provided for monitoring a user having a chronic gastrointestinal indication. A questionnaire regarding a plurality of conditions is provided on a repeating basis. Each such condition at least partly arises from the gastrointestinal indication. Questionnaire questions are each associated with a corresponding condition and provide an affordance that allows the user to select between low and high values in accordance with user association with the (Continued)

condition. Responses are stored in a data store associated with the user. A user requested report comprising a graphical quality of life measure of the user is provided based upon temporal questionnaire answers. Questionnaire information is communicated to a remote device for medical practitioner evaluation and computation of a temporal overall quality of life score based on a plurality of component quality of life scores, each of which is associated with a condition in the plurality of conditions.

21 Claims, 39 Drawing Sheets

(51) Int. Cl.
| | | |
|---|---|---|
| G16H 20/10 | (2018.01) | |
| G16H 20/70 | (2018.01) | |
| G16H 40/67 | (2018.01) | |
| G16H 40/20 | (2018.01) | |
| G16H 50/50 | (2018.01) | |
| A61B 5/00 | (2006.01) | |
| A61B 5/11 | (2006.01) | |
| G08B 7/06 | (2006.01) | |
| G08B 21/18 | (2006.01) | |
| G09B 19/00 | (2006.01) | |
| G06F 3/0482 | (2013.01) | |
| G06F 3/04847 | (2022.01) | |

(52) U.S. Cl.
CPC .......... *A61B 5/4238* (2013.01); *A61B 5/4255* (2013.01); *A61B 5/4824* (2013.01); *A61B 5/742* (2013.01); *A61B 5/746* (2013.01); *G08B 7/06* (2013.01); *G08B 21/182* (2013.01); *G09B 19/00* (2013.01); *G16H 15/00* (2018.01); *G16H 20/10* (2018.01); *G16H 20/70* (2018.01); *G16H 40/20* (2018.01); *G16H 40/67* (2018.01); *G16H 50/50* (2018.01); *G06F 3/0482* (2013.01); *G06F 3/04847* (2013.01)

(58) Field of Classification Search
CPC ..... G16H 20/70; A61B 5/0022; A61B 5/1118; A61B 5/411; A61B 5/4238; A61B 5/4824; A61B 5/742; A61B 5/746; G08B 7/06; G08B 21/182; G09B 19/00; G06F 3/0482; G06F 3/04847
USPC .......................................................... 705/2
See application file for complete search history.

(56) References Cited

U.S. PATENT DOCUMENTS

| | | | |
|---|---|---|---|
| 2009/0043609 A1 | 2/2009 | Nadas et al. | |
| 2009/0240115 A1* | 9/2009 | Bluth | G06Q 40/00 600/300 |
| 2011/0184250 A1 | 7/2011 | Schmidt et al. | |
| 2013/0035951 A1* | 2/2013 | Frey | G16H 50/30 600/300 |
| 2013/0262155 A1 | 10/2013 | Hinkamp | |
| 2014/0046682 A1 | 2/2014 | Soto et al. | |
| 2014/0257852 A1* | 9/2014 | Walker | G06Q 10/10 705/3 |
| 2016/0004820 A1* | 1/2016 | Moore | G16H 15/00 705/3 |
| 2016/0063205 A1* | 3/2016 | Moturu | G16H 40/67 705/3 |
| 2016/0379511 A1* | 12/2016 | Dawson | G06T 11/206 434/362 |

OTHER PUBLICATIONS

A. Honka et al., "Rethinking Health: ICT-Enabled Services to Empower People to Manage Their Health," in IEEE Reviews in Biomedical Engineering, vol. 4, pp. 119-139, 2011, doi: 1109/RBME.2011.2174217. (Year: 2011).*
Atreja, A., et al., "HealthPROMISE: Utilization of Patient Reported Outcomes to Measure Quality of Life in Inflammatory Bowel isease", iproc 2017;3(1):e28).
Gunerhanal, B.R., et al., "Is Digital Health Intervention Effective in Inflammatory Bowel Disease Patients?", Komp Nutr Diet 2021;1:95-96, 2021.
International Search Report and Written Opinion for International Patent Application No. PCT/US2017/018503, dated May 25, 2017, 12 pages.
Allen et al., "Adult Inflammatory Bowel Disease Physician Performance Measures Set", American Gastroenterological Association, Mar. 4, 2010.
Atreja et al., "Impact of the Mobile HealthPROMISE Platform on the Quality of Care and Quality of Life in Patients with Inflammatory Bowel Disease: Study Protocol of a Pragmatic Randomized Controlled Trial", JMIR Res Protoc. Jan.-Mar. 2015; 4(1): e23; Published online Feb. 18, 2015. doi: 10.2196/resprot.4042: 10.2196/resprot.4042.
Chen et al., "Costs of Quality Improvement: A Survey of Four Acute Care Hospitals", Jt Comm J Qual Patient Saf. Nov. 2009;35(11):544-50.
Cohen, "The quality of life in patients with Crohn's disease", Aliment Pharmacol Ther. Sep. 2002;16(9):1603-9.
Cretin et al., "An evaluation of collaborative interventions to improve chronic illness care. Framework and study design", Eval Rev. Feb.: 28(1):28-51, doi:10.1177/0193841X03256298 (PubMed: 14750290).
Hibbard et al., "Development and testing of a short form of the patient activation measure", Health Serv Res. Dec. 2005; 40(6 Pt 1): 1918-1930.
Irvine et al., "The Short Inflammatory Bowel Disease Questionnaire: a quality of life instrument for community physicians managing inflammatory bowel disease. CCRPT Investigators. Canadian Crohn's Relapse Prevention Trial", Am J Gastroenterol. Aug. 1996;91(8):1571-8.
Irvine, "Quality of life issues in patients with inflammatory bowel disease", Am J Gastroenterol. Dec. 1997;92(12 Suppl):18S-24S.
Norman et al., "eHEALS: The eHealth Literacy Scale", J Med Internet Res., Oct.-Dec. 2006; 8(4): e27.
Rabin and Charro, "EQ-5D: a measure of health status from the EuroQol Group", Ann Med 2001;33: 337-343.
Wagner, "Chronic Disease Management: What will it take to Improve Care for Chronic Illness?", Eff Clin Pract. 1(1):2-4, 1998.

* cited by examiner

Questionnaire: IBD Quality of Life ▼    ⦿ Add Question    Cancel

Questions

| Type | Question | |
|---|---|---|
| 7PointSlider | How often has the feeling of fatigue or of being tired and worn out been a problem for you the last 2 weeks? | ⊙ |
| 7PointSlider | How often during the last 2 weeks have you had to delay or cancel a social engagement because of your bowel problem? | ⊙ |
| 7PointSlider | How much difficulty have you had as a result of your bowel problem doing leisure or sports activities you would have liked to...? | ⊙ |
| 7PointSlider | How often during the last 2 weeks have you been troubled by pain in the abdomen? | ⊙ |
| 7PointSlider | How often during the last 2 weeks have you felt depressed or discouraged? | ⊙ |
| 7PointSlider | Overall, in the last 2 weeks, how much of a problem have you had passing large amounts of gas? | ⊙ |
| 7PointSlider | Overall, in the last 2 weeks, how much of a problem have you had maintaining or getting to the weight you would like to be? | ⊙ |
| 7PointSlider | How often during the last 2 weeks have you felt relaxed and free of tension? | ⊙ |
| 7PointSlider | How much of the time during the last 2 weeks have you been troubled by a feeling of having to go to the toilet even though...? | ⊙ |
| 7PointSlider | How much of the time during the last 2 weeks have you felt angry as a result of your bowel problem? | ⊙ |

Add Question

Question Details
- Type*: 7PointSlider ▶
- Question*: [         ]

Option Details
1.*
2.*
3.*
4.*
5.*
6.*
7.*

[Save]
[Cancel]

| QOL Category | | |
|---|---|---|
| Name | | |
| Heartburn | ✏️ | ⊖ |
| Pain | ✏️ | ⊖ |
| Frequency of BMs | ✏️ | ⊖ |
| Anxiety | ✏️ | ⊖ |
| Depression | ✏️ | ⊖ |
| Diarrhea | ✏️ | ⊖ |
| Blood in Stool | ✏️ | ⊖ |
| Appetite | ✏️ | ⊖ |
| Fatigue | ✏️ | ⊖ |
| Sleep Disturbance | ✏️ | ⊖ |

⊙ Add

Fig. 5E

| Checklist | |
|---|---|
| Name | Description |
| Bone Density Test | Bone density test such as Dual-energy X-ray absoptometry (DEXA) is a means of measuring bone mineral de... |
| Normal Mucus on End... | My provider informed me that my small or large bowel mucus during endoscopy is normal, this is free from infla... |
| Colonoscopy | Colon screeing test recommended almost once every two years for patients who have Crohns or Colitis for mor... |
| Vaccination for Flu | Annual Flu vaccination is recommended for all Crohns and Colitis patients. |
| Vaccination for Pneu... | Pneumonia Vaccine is recommended at least once every 5 years for patients with Crohns or Colitis. |
| Smoking Cessation Ad... | If you are a smoker, have you been offered cessation (quitting) guidance by your physician treating IBD? |
| Oral Medication Adher... | Considered Met if you took your oral IBD medications most of the time as recommended by your physician. |
| Steroid spaning medic... | For patients on steroids, physicians recommend immunomodulators like 6MP, Azathioprine, Methotrexate or bi... |
| Tuberculosis Test | ONLY for patients on Biologics (Remedide, Cimgia, Humira, Simponil, Stelara, Ertyvia), it is recommended to b... |
| Hepatitis & Screening | ONLY for patients taking Biologics (Remedide, Cimgia, Humira, Simponil, Stelara, Ertyvia), it is recommended t... |
| Skin Cancer Protection | Has your physician treating IBD spoken to you about their recommendationas to reduce skin cancer risk? |
| Normal Inflammatory M... | Have you been informed by your physician that your inflammatory markers (CRP, ESR, Calprotection) are in th... |
| TPMT Testing | ONLY for patients on 6MP/Mertaptoguine Azathioprine, have you had TPMT blood testing to find the right dos...? |
| Injectable Drug Adher... | Considered Met if you took your injectable IBD medications most of the time as recommended by your physician. |
| Smoking Screening | Has the physicain treating IBD asked you within 12 months if you smoke or not? |

Fig. 5F

| Medication | | |
|---|---|---|
| Name | | |
| Humina | ✎ | ⊖ |
| Prednisone | ✎ | ⊖ |
| Azadthioprine | ✎ | ⊖ |
| Methotrexate | ✎ | ⊖ |
| Cycloporine | ✎ | ⊖ |
| Adalmumab | ✎ | ⊖ |
| Natalizumab | ✎ | ⊖ |
| Ciproflaxacin | ✎ | ⊖ |
| Metronidazole | ✎ | ⊖ |
| Infiximab | ✎ | ⊖ |
| Mesalamine | ✎ | ⊖ |
| Olselazine | ✎ | ⊖ |
| Sulfasalazine | ✎ | ⊖ |
| Balsalazide | ✎ | ⊖ |
| Cimzia | ✎ | ⊖ |
| Simponi | ✎ | ⊖ |
| Steliara | ✎ | ⊖ |
| Entyvio | ✎ | ⊖ |

⊙ Add

Add Medication

Medication

Name* [          ]

💾 Save    Cancel

Fig. 5G

SYSTEMS AND METHODS FOR MONITORING SUBJECTS HAVING CHRONIC GASTROINTESTINAL INDICATIONS

CROSS REFERENCE TO RELATED APPLICATIONS

This Application is a National Stage of International Patent Application No. PCT/US2017/143284, entitled "Systems and Methods for Monitoring Subjects Having Chronic Gastrointestinal Indications," filed Feb. 17, 2017 and published as WO 2017/142384 A1, which claims priority to U.S. Provisional Patent Application No. 62/297,720 entitled "Systems and Methods for Monitoring Subjects Having Chronic Gastrointestinal Indications," filed Feb. 19, 2016, each of which is hereby incorporated by reference.

STATEMENT REGARDING FEDERALLY SPONSORED RESEARCH OR DEVELOPMENT

Part of the work performed during development of this invention utilized U.S. Government funds through grant number K23 DK097451 of the National Institute of Health (NIH). The U.S. Government has certain rights in this invention.

TECHNICAL FIELD

The present disclosure relates generally to systems and methods for monitoring subjects having chronic gastrointestinal indications.

BACKGROUND

Measuring and improving healthcare quality is a major public health issue and a topic of considerable media attention and health policy debate. For example, despite annual expenditures exceeding $2.5 trillion, the quality of U.S. healthcare remains far from optimal. Soaring health care costs, poor quality outcomes, and increasing fragmentation of care have become the major drivers of health care reforms, including Pay for Performance, Meaningful Use and the Affordable Care Act of 2010. In order to address the three-part aim of better health, better health care, and lower costs through improved quality, national gastrointestinal societies such as the American Gastroenterological Association (AGA) and Crohn's & Colitis Foundation of America (CCFA) have started to support various quality improvement (QI) initiatives. "Digestive Health Outcomes Registry" and "Improve Care Now" are few noteworthy initiatives trying to improve the quality of care delivered to patients with inflammatory bowel disease. While adoption of these solutions is fast growing, there is a pressing need for solutions that are effective (improves outcomes), generalizable (easily adopted across diverse practices) and sustainable (minimizes manual data entry, easy to maintain).

While diseases such as hypertension and diabetes render themselves well to quality improvement efforts because of standardized indicators such as blood pressure and hemoglobin AIC respectively, quality-of-care (QOC) metrics cannot easily define chronic gastrointestinal indications. The heterogeneous nature of the diseases underlying chronic gastrointestinal indications means that the optimal patient management approach differs between different phenotypes. Furthermore, chronic gastrointestinal indication such as inflammatory bowel disease (IBD) profoundly affects patients not only physically but also in social, professional, and emotional activities. See for example, Cohen 2002, "The quality of life in patients with Crohn's disease," Aliment Pharmacol Ther. 9:1603-1609; Irvine, 1997, "Quality of life issues in patients with inflammatory bowel disease," Am J Gastroenterol. 92 (12 Suppl) 18S-24S; and Atreja et al., 2015 "Impact of the Mobile HealthPROMISE Platform on the Quality of Care and Quality of Life in Patients with Inflammatory Bowel Disease: Study Protocol of a Pragmatic Randomized Controlled Trial," JMIR Res Protocol 4(1): e23, each of which is hereby incorporated by reference herein in its entirety. Overall wellbeing of such patients cannot be achieved if these dimensions are not improved. Unfortunately, conventional quality improvement initiatives are process measures and do not include quality of life or clinically meaningful outcomes such as clinical remission or hospitalizations that matter most to patients and their state of health.

Chronic diseases affect almost 1 out of every 2 Americans and produce a significant burden on United States health care. Meaningful health system quality improvement warrants patient-provider interaction focused on quality of care and quality of life in chronic gastrointestinal indications like IBD. Thus, what is needed in the art are better, more economical, ways to engage patients with chronic gastrointestinal indications without placing increased time constraints on health care staff. Thus, given the above background, what is need in the art are improved, economical systems and methods for monitoring subjects having chronic gastrointestinal indications.

SUMMARY

The present disclosure addresses the need in the art for better, more economical ways to engage patients having chronic gastrointestinal indications without placing increased time constraints on health care staff. Advantageously, the disclosed systems and methods enable patient self-reporting in order to compute quality of life metrics without the mandatory requirement of a medical visit to a medical practitioner. In this way, meaningful quality of life metrics can be computed and tracked, and used to provide patient intervention when necessary. The disclosed systems and methods guide patients with chronic gastrointestinal indications in an economical way, improve their quality of life and quality of care, and reduce overall medical costs of treatment of such patients.

In one embodiment, the disclosed systems and methods address the need in the art for improved systems and methods for monitoring subjects having chronic gastrointestinal indications. A questionnaire regarding a plurality of conditions is provided on a repeating basis to a subject having a chronic gastrointestinal indication. Each such condition at least partly arises from the gastrointestinal indication. Questionnaire questions are each associated with a corresponding condition and provide a subject with an affordance that allows the subject to select between low and high values in accordance with subject association with the condition. Responses are stored in a data store associated with the subject. A user requested report comprising a graphical quality of life measure of the subject is provided based upon temporal questionnaire answers. Questionnaire information is communicated to a remote device for medical practitioner evaluation and computation of a temporal overall quality of life score based on a plurality of component quality of life scores, each of which is associated with a condition in the plurality of conditions.

In one aspect, the present disclosure provides methods in which, at an Internet-enabled electronic device with a display, and while running an application on the device, there is provided, on a repeating basis over a period of time, a questionnaire within the application regarding a plurality of conditions. Each such condition arises, at least in part, from a chronic gastrointestinal indication associated with a subject. The questionnaire comprises a plurality of questions. Each respective question in the plurality of questions is associated with a corresponding condition in the plurality of conditions. Each respective question in the plurality of questions comprises an affordance that is configured to allow the subject to select between a low value and a high value to indicate a degree to which the subject presently associates with the condition corresponding to the respective question. Advantageously, the application also allows reporting of data captured automatically (without human intervention) from the Internet-enabled electronic device (e.g., activity, sleep cycle, etc.). In some such embodiments, the application interfaces with other applications on the device that collect such information. In some such embodiments, the application interfaces with devices worn by the subject (e.g., wearable biometric devices) that collect such information.

In accordance with the disclosed methods, subject responses to the questionnaire are stored in a data store associated with the subject in the electronic device each time the subject responds to the questionnaire. Responsive to a report request from the subject, the disclosed methods provide such a subject report within the application. The report comprises a graphical quality of life measure of the subject as a function of time based upon answers to the plurality of questions in the questionnaire over the period of time. The graphical quality of life measure incorporates a subjective assessment, made by the subject, of a social factor affected by the chronic gastrointestinal indication and an objective assessment of an illness factor associated with the gastrointestinal indication.

In accordance with the disclosed systems and methods, information in the data store associated with the subject from the questionnaire is communicated to a remote device for evaluation by a medical practitioner. In this way, the disclosed systems and methods facilitate remote monitoring of patients. Providers or health systems can delegate regular monitoring of patient data received by the disclosed systems and methods to personnel who can monitor patients closely and alert providers as needed. As disclosed herein, in some embodiments the disclosed systems and methods also trigger alerts when certain conditions are met or unmet. Communication of such alerts to delegated medical personnel further facilitates automated remote monitoring of subjects.

In some embodiments, the information that is communicated to a remote device for evaluation by a medical practitioner is formatted for computation of an overall quality of life score for the subject, over the period of time, based on a plurality of component quality of life scores. Each component quality of life score in the plurality of component quality of life scores is associated with at least one condition in the plurality of conditions.

In some embodiments, a psychosocial intervention request is received from the remote device. Responsive to receiving the psychosocial intervention request, a psychosocial interaction activity is provided to the subject within the application. Examples of psychosocial interaction activities include, but are not limited to, instructions on how to self-administer an injectable, a relaxation technique, instructions on sleep hygiene, instructions for performing an exercise to manage fatigue, or instructions on anger control. In some embodiments, these instructions are in the form of a video, a picture, a document, or a uniform resource location link to a document.

In some embodiments, the plurality of conditions comprises anxiety, fatigue, social discomfort, leisure, stress level, abdomen pain, depression, gas, weight maintenance, tension, bowel incident, and anger.

In some embodiments, the low value is a numerical "1" indicating that the subject does not associate with the corresponding condition and the high value is a numerical "10" indicating the subject highly associates with the corresponding condition.

In some embodiments, the providing the questionnaire is done on a recurring basis (e.g., between two and ten days). In some embodiments, the subject report further comprises a condition plot as a function of time derived from the responses to the questionnaire. In some embodiments, the report further comprises a checklist of care indicating a number of care tasks associated with the chronic gastrointestinal indication the subject has completed. In some embodiments, the subject report further comprises an indication of a number of hospital and emergency room visits the subject has participated in during a predetermined period of time (e.g., the past three months).

In some embodiments, the chronic gastrointestinal indication is inflammatory bowel disease (e.g., Crohn's disease, ulcerative colitis, or indeterminate colitis). In some embodiments, the chronic gastrointestinal indication is obesity or irritable bowel syndrome. In some embodiments, the subject has undergone a bariatric surgical procedure to alleviate the chronic gastrointestinal condition. In some embodiments, the bariatric surgical procedure comprises a gastric bypass, a sleeve gastrectomy, insertion of an adjustable gastric band, or a biliopancreatic diversion with duodenal switch.

In some embodiments, the chronic gastrointestinal indication is gastrointestinal neoplasia, Celiac disease, a food allergy (e.g., allergy to cow's milk, eggs, fish, peanuts, shell fish, soy, tree nuts, wheat, etc.) or a food intolerance (e.g., intolerance to lactose, sucrose, maltose, histamine, tyramine, salicylate, tartrazine, benzoates, monosodium glutamate, a food dye, etc.).

In some embodiments, the Internet-enabled electronic device is a tablet or smart phone. In some embodiments, the report further comprises a visual representation of resource utilization. In some embodiments, the graphical quality of life measure is interactive and includes instructions for providing the subject an action plan based upon the graphical quality of life measure upon request of the subject.

In some embodiments, the Internet-enabled electronic device further comprises an alerts lookup table comprising a plurality of alerts. Each such alert comprises a corresponding trigger condition in a plurality of trigger conditions and an action in a plurality of actions. In such embodiments, the application compares the quality of life score of the subject on a temporal basis with each trigger condition of each alert in the alerts lookup table. When the quality of life score of the subject on the temporal basis matches a trigger condition of a first alert in the plurality of alerts, the corresponding action of the first alert is fired. In some embodiments, the trigger condition for the first alert is a drop in the quality of life score by a predetermined amount over a predetermined amount of time and the first alert is a notification to the subject, through the application, for follow up care or appointment scheduling with a medical practitioner. In some embodiments, firing of the first alert comprises initiating a visual alert, an audible alert or a vibrational alert.

In some embodiments, the graphical quality of life measure is color coded using a color schema. In such embodiments, each color in the color schema indicates a different quality of life tertile.

In some embodiments, the affordance of a question in the plurality of questions is a slide bar that is configured to be moved by the subject to any one of a predetermined number of positions between and inclusive of the low value and the high value to indicate a degree to which the subject presently associates with the corresponding condition. In some embodiments, the predetermined number of positions is three, four, five, six, seven, eight, nine, ten, eleven, or twelve.

In some embodiments, the social factor comprises a mood of the subject, an anxiety level of the subject, a depression level of the subject, an amount of pain incurred by the subject, or fatigue incurred by the subject and the illness factor comprises a number of bowel movements per day incurred by the subject.

In some embodiments, the plurality of questions in the questionnaire includes a mobility query, a self-care query, and an activity query.

In some embodiments, the application further comprises a medication module that tracks one or more medicines that the subject is taking to alleviate the chronic gastrointestinal indication. In some embodiments, the application further comprises an allergy module that tracks one or more allergies associated with the subject.

In some embodiments, usage of the application by the subject reduces a propensity of the subject to require live medical practitioner care during the period of time by a threshold amount (by at least ten percent, by at least twenty percent, by at least thirty percent, by at least forty percent, by at least fifty percent, by at least sixty percent, by at least seventy percent, by at least eighty percent) relative to subjects having the chronic gastrointestinal indication that do not use the application. In some embodiments, the live medical practitioner is in the form of an outpatient doctor visit, ambulatory care, or emergency room visit. In some such embodiments, the threshold amount is at least 10 percent, at least 20 percent, at least 30 percent, at least 40 percent, or at least fifty percent. In some embodiments, a cost associated with treatment of the subject during the period of time is reduced by at least 10 percent, at least 20 percent, at least 30 percent, at least 40 percent, or at least fifty percent by the subject's usage of the application.

In some embodiments, the affordance is a slide bar, an input field, a plurality of radio buttons, or a drop-down menu.

Another aspect of the present disclosure provides a non-transitory computer readable storage medium for monitoring a chronic gastrointestinal indication. The non-transitory computer readable storage medium stores instructions, which when executed by a first Internet-enabled device, cause the first Internet-enabled device to perform any of the methods disclosed herein.

Still another aspect of the present disclosure is an Internet-enabled computer system, comprising one or more processors memory; and one or more programs stored in the memory for execution by the one or more processors. The one or more programs comprising instructions for performing any of the methods disclosed herein.

BRIEF DESCRIPTION OF THE DRAWINGS

FIGS. 5A, 5B, 5C, 5D, 5E, 5F, and 5G collectively provide a flow chart of processes and features of a system for monitoring subjects having a chronic gastrointestinal indication in accordance with an embodiment of the present disclosure.

Like reference numerals refer to corresponding parts throughout the several views of the drawings.

DETAILED DESCRIPTION

Reference will now be made in detail to embodiments, examples of which are illustrated in the accompanying drawings. In the following detailed description, numerous specific details are set forth in order to provide a thorough understanding of the present disclosure. However, it will be apparent to one of ordinary skill in the art that the present disclosure may be practiced without these specific details. In other instances, well-known methods, procedures, components, circuits, and networks have not been described in detail so as not to unnecessarily obscure aspects of the embodiments.

It will also be understood that, although the terms first, second, etc. may be used herein to describe various elements, these elements should not be limited by these terms. These terms are only used to distinguish one element from another. For example, a first subject could be termed a second subject, and, similarly, a second subject could be termed a first subject, without departing from the scope of the present disclosure. The first subject and the second subject are both subjects, but they are not the same subject. Furthermore, the terms "subject" and "user" are used interchangeably herein.

The terminology used in the present disclosure is for the purpose of describing particular embodiments only and is not intended to be limiting of the invention. As used in the description of the invention and the appended claims, the singular forms "a", "an" and "the" are intended to include the plural forms as well, unless the context clearly indicates otherwise. It will also be understood that the term "and/or" as used herein refers to and encompasses any and all possible combinations of one or more of the associated listed items. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

As used herein, the term "if" may be construed to mean "when" or "upon" or "in response to determining" or "in response to detecting," depending on the context. Similarly, the phrase "if it is determined" or "if [a stated condition or event] is detected" may be construed to mean "upon determining" or "in response to determining" or "upon detecting [the stated condition or event]" or "in response to detecting [the stated condition or event]," depending on the context.

Figure 1:
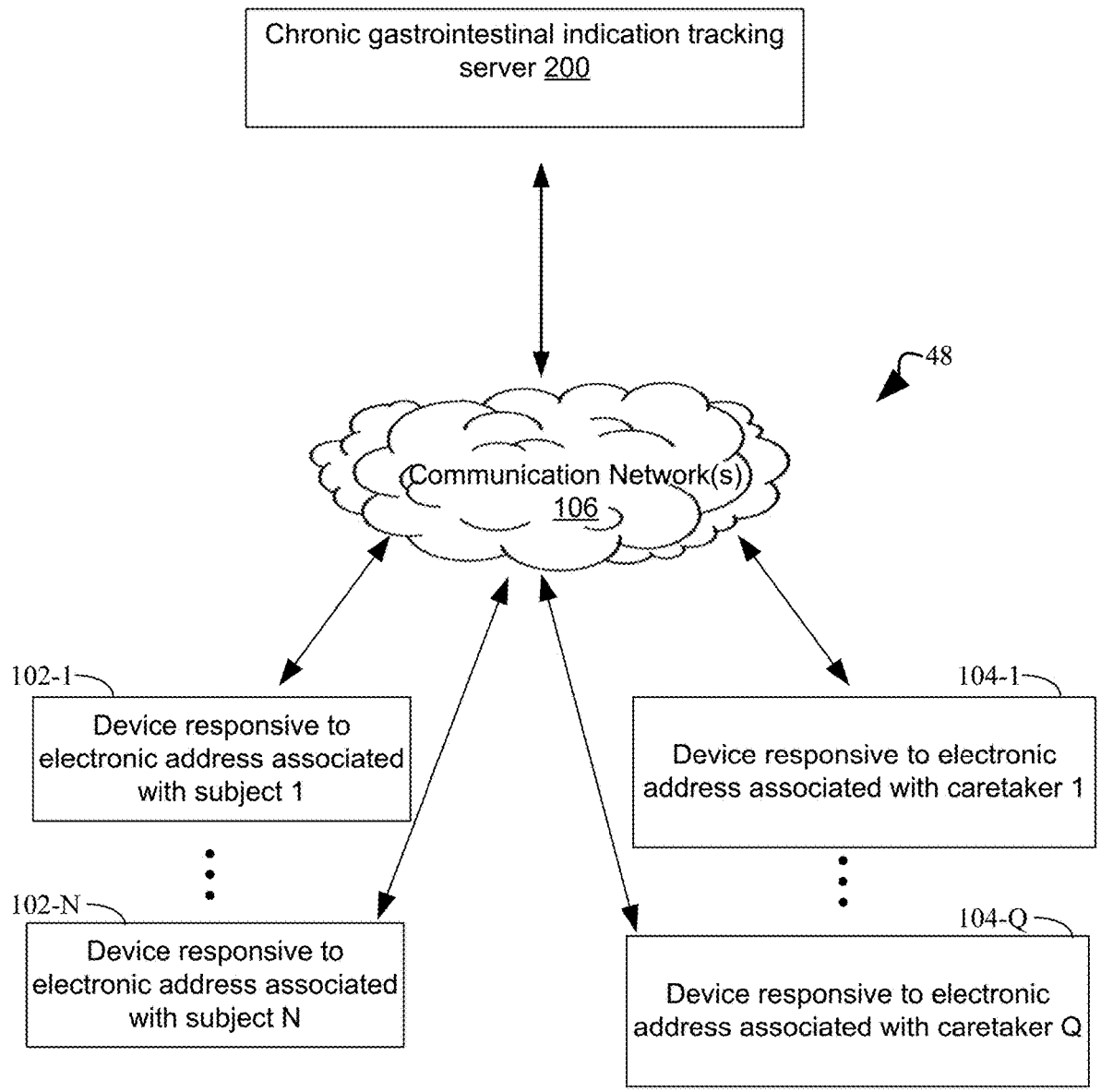
FIG. 1 illustrates a system topology in accordance with the present disclosure that includes a chronic gastrointestinal indication tracking server, a plurality of devices associated with subjects that are being monitored, and devices that are associated with medical professionals.
Figure 2:
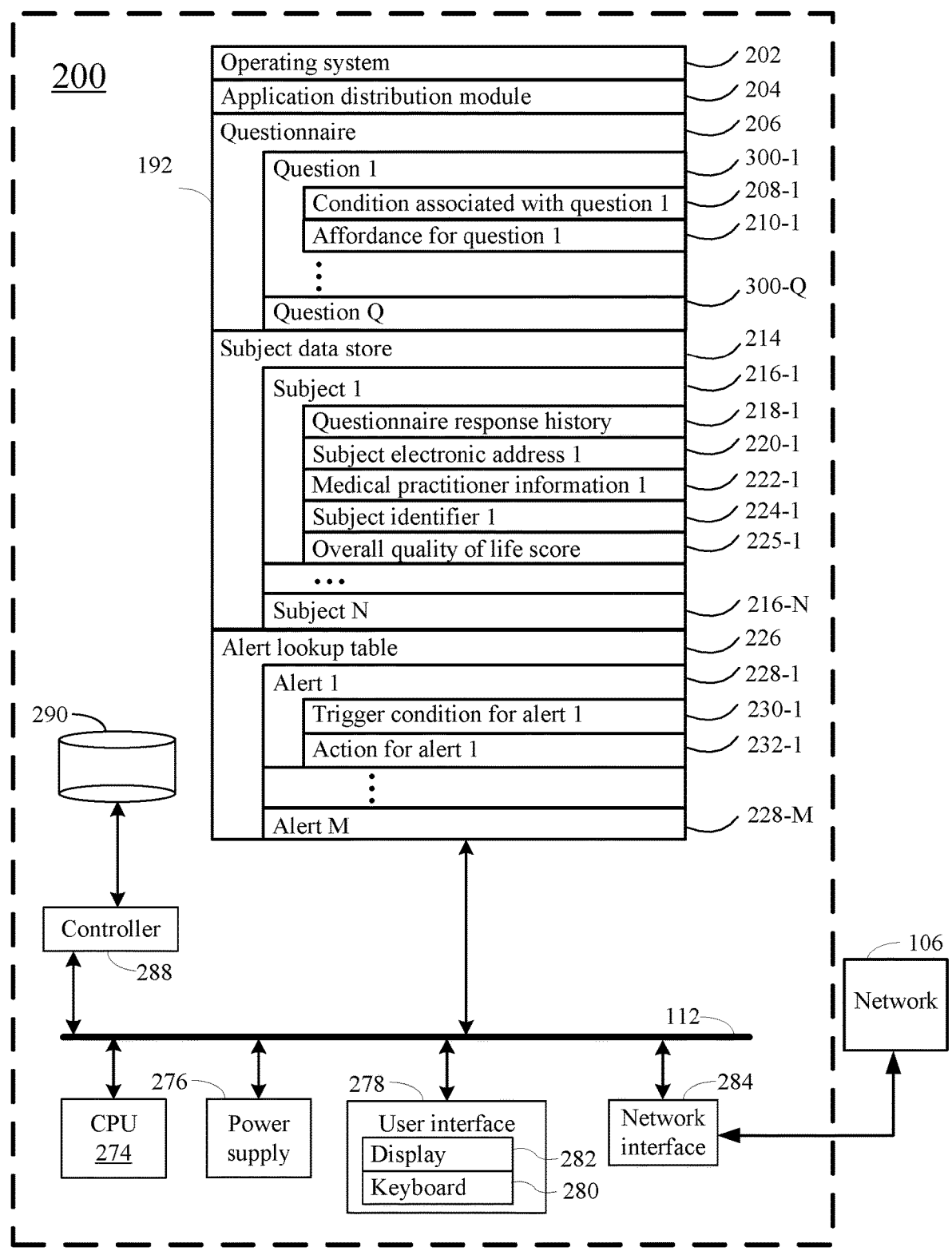
FIG. 2 illustrates a chronic gastrointestinal indication tracking server in accordance with an embodiment of the present disclosure.
Figure 3:
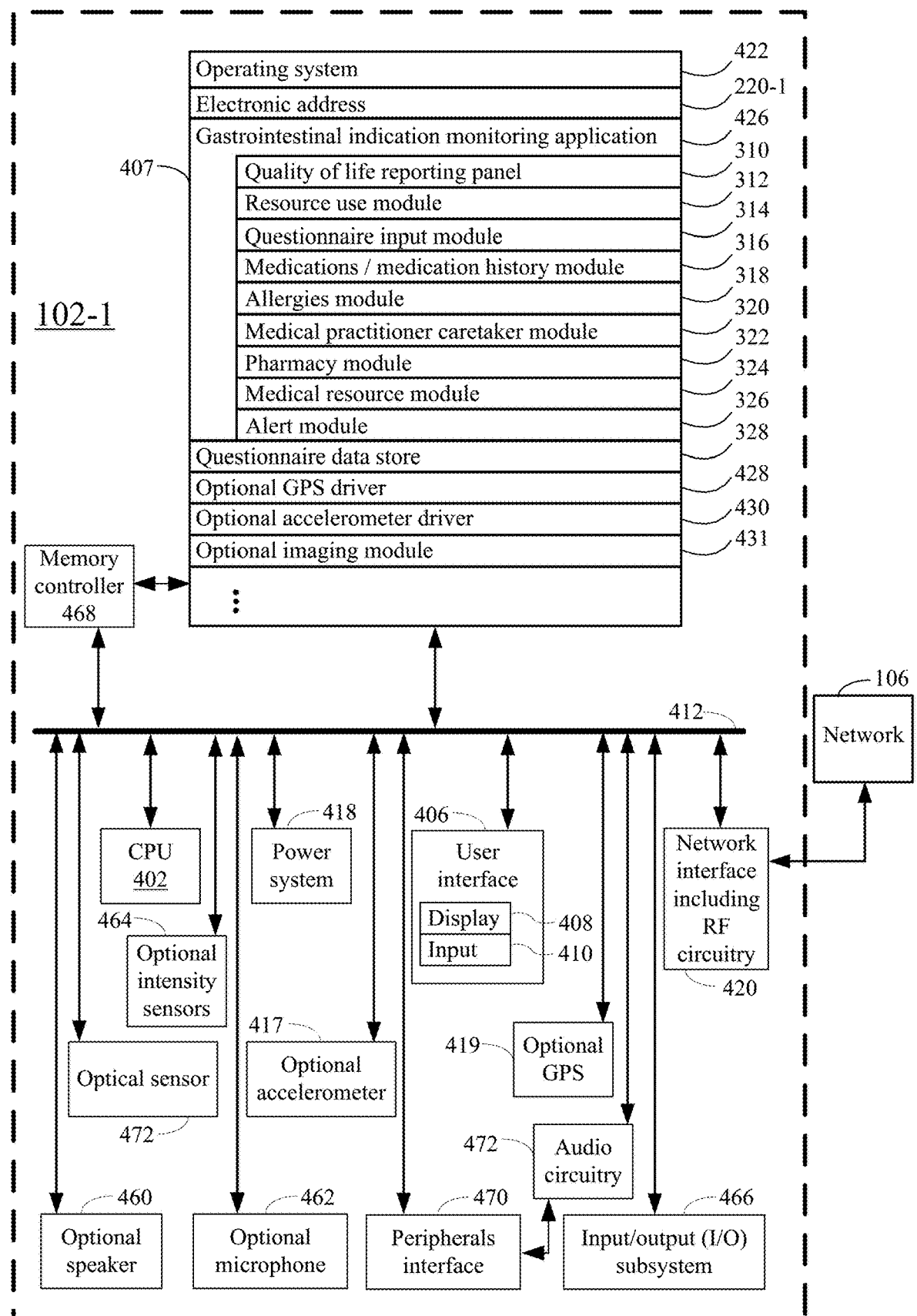
FIG. 3 illustrates a device associated with a subject that is being monitored, in accordance with an embodiment of the present disclosure.
Figure 4:
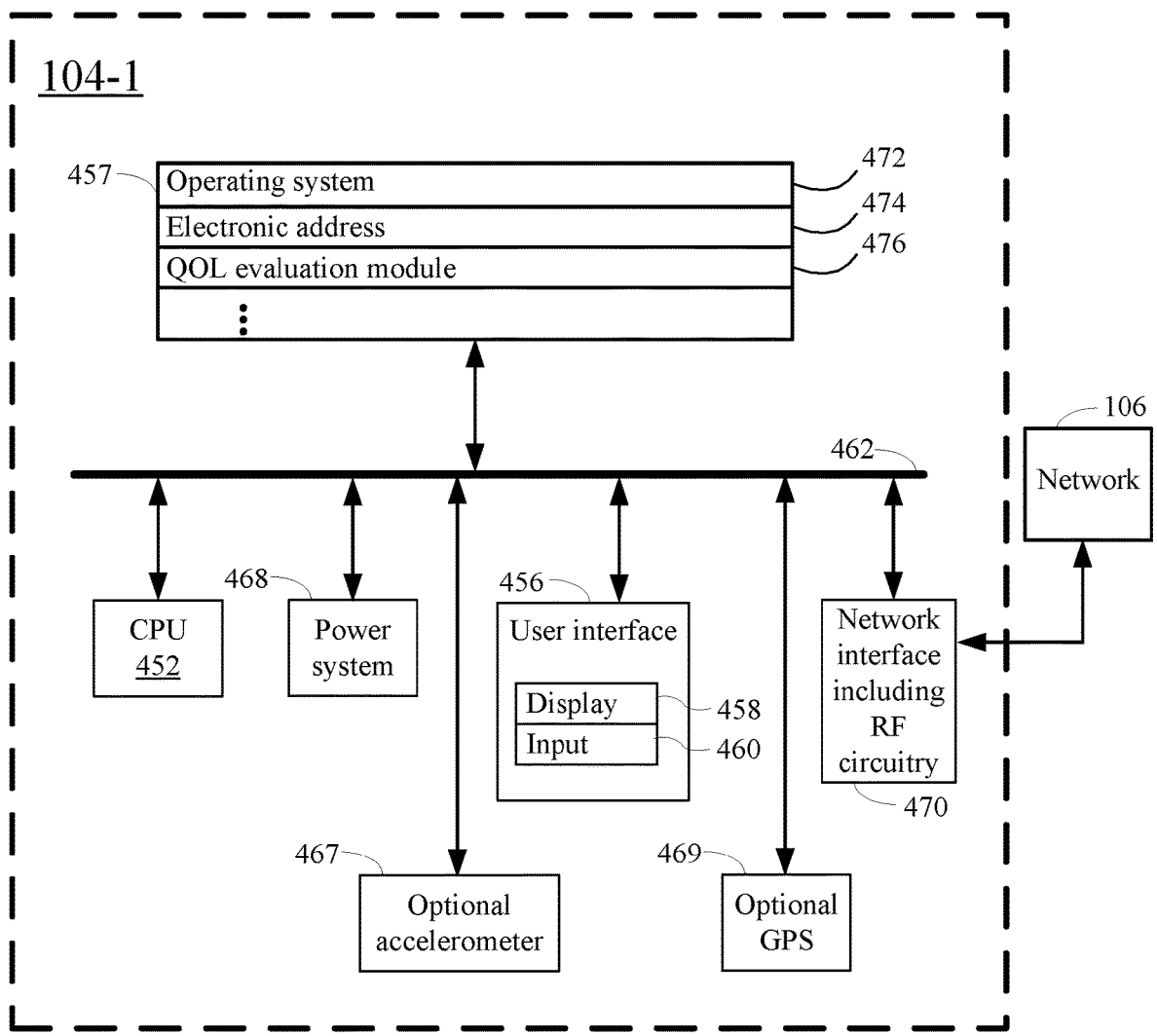
FIG. 4 illustrates a device associated with a medical professional or other form of caretaker, in accordance with an embodiment of the present disclosure.

A detailed description of a system 48 for monitoring a subject having a chronic gastrointestinal indication in accordance with the present disclosure is described in conjunction with FIGS. 1 through 4. As such, FIGS. 1 through 4 collectively illustrate the topology of the system in accordance with the present disclosure. In the topology, there is a chronic gastrointestinal indication tracking server 200 (FIGS. 1 and 2), devices 102 responsive to electronic addresses associated with subjects to be monitored (FIGS. 1 and 3), and devices 104 responsive to the electronic addresses associated with caretakers (FIGS. 1 and 4).

Of course, other topologies of system 48 are possible, for instance, chronic gastrointestinal indication tracking server 200 can in fact constitute several computers that are linked together in a network or be a virtual machine in a cloud computing context. As such, the exemplary topology shown in FIG. 1 merely serves to describe the features of an embodiment of the present disclosure in a manner that will be readily understood to one of skill in the art.

Referring to FIG. 2, in typical embodiments, a chronic gastrointestinal indication tracking server 200 comprises one or more computers. For purposes of illustration in FIG. 2, the chronic gastrointestinal indication tracking server 200 is represented as a single computer that includes all of the functionality of the chronic gastrointestinal indication tracking server 200. However, the disclosure is not so limited. The functionality of the chronic gastrointestinal indication tracking server 200 may be spread across any number of networked computers and/or reside on each of several networked computers and/or by hosted on one or more virtual machines at a remote location accessible across the communications network 106. One of skill in the art will appreciate that a wide array of different computer topologies are possible for the chronic gastrointestinal indication tracking server 200 and all such topologies are within the scope of the present disclosure.

Turning to FIG. 2 with the foregoing in mind, an exemplary chronic gastrointestinal indication tracking server 200 comprises one or more processing units (CPU's) 274, a network or other communications interface 284, a memory 192 (e.g., random access memory), one or more magnetic disk storage and/or persistent devices 290 optionally accessed by one or more controllers 288, one or more communication busses 112 for interconnecting the aforementioned components, and a power supply 276 for powering the aforementioned components. Data in memory 192 can be seamlessly shared with non-volatile memory 290 using known computing techniques such as caching. Memory 192 and/or memory 290 can include mass storage that is remotely located with respect to the central processing unit(s) 274. In other words, some data stored in memory 192 and/or memory 290 may in fact be hosted on computers that are external to chronic gastrointestinal indication tracking server 200 but that can be electronically accessed by the chronic gastrointestinal indication tracking server over an Internet, intranet, or other form of network or electronic cable (illustrated as element 106 in FIG. 2) using network interface 284.

The memory 192 of chronic gastrointestinal indication tracking server 200 stores:

- an operating system 202 that includes procedures for handling various basic system services;
- an application module 204 for distributing an application to a plurality of subjects having a chronic gastrointestinal indication;
- a questionnaire 206 that includes a plurality of questions, each respective question 300 in the plurality of questions (i) is associated with a corresponding condition 208 in a plurality of conditions associated with the chronic gastrointestinal indication and (ii) comprises an affordance 210 that is configured to allow the subject to select between a low value and a high value to indicate a degree to which the subject presently associates with the corresponding condition;
- a subject data store 214, the subject data store comprising a respective record of each corresponding subject 216 monitored by the disclosed systems, each respective record including (i) a questionnaire response history 218 from the corresponding subject, (ii) one or more electronic addresses 220 associated with the corresponding subject, (iii) medical practitioner contact information 222, (iv) an optional unique subject identifier 224 associated with the corresponding subject for the corresponding subject, and (v), an overall quality of life score 225 for the corresponding subject; and
- an alert lookup table 226 comprising a plurality of alerts, each respective alert 228 in the alert data store 226 comprising one or more trigger conditions 230 and one or more actions 232.

In some implementations, one or more of the above identified data elements or modules of the chronic gastrointestinal indication tracking server 200 are stored in one or more of the previously described memory devices, and correspond to a set of instructions for performing a function described above. The above identified data, modules or programs (e.g., sets of instructions) need not be implemented as separate software programs, procedures or modules, and thus various subsets of these modules may be combined or otherwise re-arranged in various implementations. In some implementations, the memory 192 and/or 290 optionally stores a subset of the modules and data structures identified above. Furthermore, in some embodiments the memory 192 and/or 206 stores additional modules and data structures not described above.

In some embodiments, a device 102 responsive to an electronic address 220 of subject 216 is a smart phone (e.g., an iPHONE), laptop, tablet computer, desktop computer, or other form of electronic device (e.g., a gaming console). In some embodiments, a device 102 is not mobile. In some embodiments, a device 102 is mobile.

FIG. 3 provides a description of a device 102 that can be used with the instant disclosure. It has one or more processing units (CPU's) 402, peripherals interface 470, memory controller 468, a network or other communications interface 420, a memory 407 (e.g., random access memory), a user interface 406, the user interface 406 including a display 408 and input 410 (e.g., keyboard, keypad, touch screen), an optional accelerometer 417, an optional GPS 419, optional audio circuitry 472, an optional speaker 460, an optional microphone 462, one or more optional intensity sensors 464 for detecting intensity of contacts on the device 102 (e.g., a touch-sensitive surface such as a touch-sensitive display system 408 of the device 102), optional input/output (I/O) subsystem 466, one or more optional optical sensors 472, one or more communication busses 412 for interconnecting the aforementioned components, and a power system 418 for powering the aforementioned components.

In some embodiments, the input 410 is a touch-sensitive display, such as a touch-sensitive surface. In some embodiments, the user interface 406 includes one or more soft keyboard embodiments. The soft keyboard embodiments may include standard (QWERTY) and/or non-standard configurations of symbols on the displayed icons.

Device 102 optionally includes, in addition to accelerometer(s) 417, a magnetometer (not shown) and a GPS 419 (or GLONASS or other global navigation system) receiver for obtaining information concerning the location and orientation (e.g., portrait or landscape) of device 102.

It should be appreciated that device 102 is only one example of a multifunction device, and that device 102 optionally has more or fewer components than shown, optionally combines two or more components, or optionally has a different configuration or arrangement of the components. The various components shown in FIG. 3 are implemented in hardware, software, firmware, or a combination thereof, including one or more signal processing and/or application specific integrated circuits.

Memory 407 optionally includes high-speed random access memory and optionally also includes non-volatile memory, such as one or more magnetic disk storage devices, flash memory devices, or other non-volatile solid-state memory devices. Access to memory 407 by other components of device 100, such as CPU(s) 407 is, optionally, controlled by memory controller 468.

Peripherals interface 470 can be used to couple input and output peripherals of the device to CPU(s) 402 and memory 407. The one or more processors 402 run or execute various software programs and/or sets of instructions stored in memory 407 to perform various functions for device 102 and to process data.

In some embodiments, peripherals interface 470, CPU(s) 402, and memory controller 468 are, optionally, implemented on a single chip. In some other embodiments, they are, optionally, implemented on separate chips.

RF (radio frequency) circuitry 108 of network interface 420 receives and sends RF signals, also called electromagnetic signals. RF circuitry 108 converts electrical signals to/from electromagnetic signals and communicates with communications networks and other communications devices via the electromagnetic signals. RF circuitry 420 optionally includes well-known circuitry for performing these functions, including but not limited to an antenna system, an RF transceiver, one or more amplifiers, a tuner, one or more oscillators, a digital signal processor, a CODEC chipset, a subscriber identity module (SIM) card, memory, and so forth. RF circuitry 108 optionally communicates with networks 106. In some embodiments, circuitry 108 does not include RF circuitry and, in fact, is connected to network 106 through one or more hard wires (e.g., an optical cable, a coaxial cable, or the like).

Examples of networks 106 include, but are not limited to, the World Wide Web (WWW), an intranet and/or a wireless network, such as a cellular telephone network, a wireless local area network (LAN) and/or a metropolitan area network (MAN), and other devices by wireless communication. The wireless communication optionally uses any of a plurality of communications standards, protocols and technologies, including but not limited to Global System for Mobile Communications (GSM), Enhanced Data GSM Environment (EDGE), high-speed downlink packet access (HSDPA), high-speed uplink packet access (HSDPA), Evolution, Data-Only (EV-DO), HSPA, HSPA+, Dual-Cell HSPA (DC-HSPDA), long term evolution (LTE), near field communication (NFC), wideband code division multiple access (W-CDMA), code division multiple access (CDMA), time division multiple access (TDMA), Bluetooth, Wireless Fidelity (Wi-Fi) (e.g., IEEE 802.11a, IEEE 802.11ac, IEEE 802.11ax, IEEE 802.11b, IEEE 802.11g and/or IEEE 802.11n), voice over Internet Protocol (VoIP), Wi-MAX, a protocol for e-mail (e.g., Internet message access protocol (IMAP) and/or post office protocol (POP)), instant messaging (e.g., extensible messaging and presence protocol (XMPP), Session Initiation Protocol for Instant Messaging and Presence Leveraging Extensions (SIMPLE), Instant Messaging and Presence Service (IMPS)), and/or Short Message Service (SMS), or any other suitable communication protocol, including communication protocols not yet developed as of the filing date of this document.

In some embodiments, audio circuitry 472, speaker 460, and microphone 462 provide an audio interface between a subject and device 102. The audio circuitry 472 receives audio data from peripherals interface 470, converts the audio data to an electrical signal, and transmits the electrical signal to speaker 460. Speaker 460 converts the electrical signal to human-audible sound waves. Audio circuitry 472 also receives electrical signals converted by microphone 462 from sound waves. Audio circuitry 472 converts the electrical signal to audio data and transmits the audio data to peripherals interface 470 for processing. Audio data is, optionally, retrieved from and/or transmitted to memory 407 and/or RF circuitry 420 by peripherals interface 470.

In some embodiments, power system 418 optionally includes a power management system, one or more power sources (e.g., battery, alternating current (AC)), a recharging system, a power failure detection circuit, a power converter or inverter, a power status indicator (e.g., a light-emitting diode (LED)) and any other components associated with the generation, management and distribution of power in portable devices.

In some embodiments, the device 102 optionally also includes one or more optical sensors 472. Optical sensor(s) 472 optionally include charge-coupled device (CCD) or complementary metal-oxide semiconductor (CMOS) phototransistors. Optical sensor(s) 472 receive light from the environment, projected through one or more lens, and converts the light to data representing an image. In conjunction with imaging module 431 (also called a camera module), optical sensor(s) 472 optionally capture still images and/or video. In some embodiments, an optical sensor is located on the back of device 102, opposite display system 408 on the front of the device, so that the touch screen is enabled for use as a viewfinder for still and/or video image acquisition. In some embodiments, another optical sensor 472 is located on the front of the device 102 so that the subject's image is obtained (e.g., to verify the health or condition of the subject, or to help diagnose a subject's condition remotely, etc.).

As illustrated in FIG. 3, a device 102 preferably comprises an operating system 422 that includes procedures for handling various basic system services. Operating system 422 (e.g., iOS, DARWIN, RTXC, LINUX, UNIX, OS X, WINDOWS, or an embedded operating system such as VxWorks) includes various software components and/or drivers for controlling and managing general system tasks (e.g., memory management, storage device control, power management, etc.) and facilitates communication between various hardware and software components.

A device 102 further comprises an electronic address 220 (a mobile phone number, social media account, or e-mail address) associated with the corresponding subject that is used by the chronic gastrointestinal indication tracking server 200 to identify subjects and questionnaire answers submitted by subjects.

Figure 6:
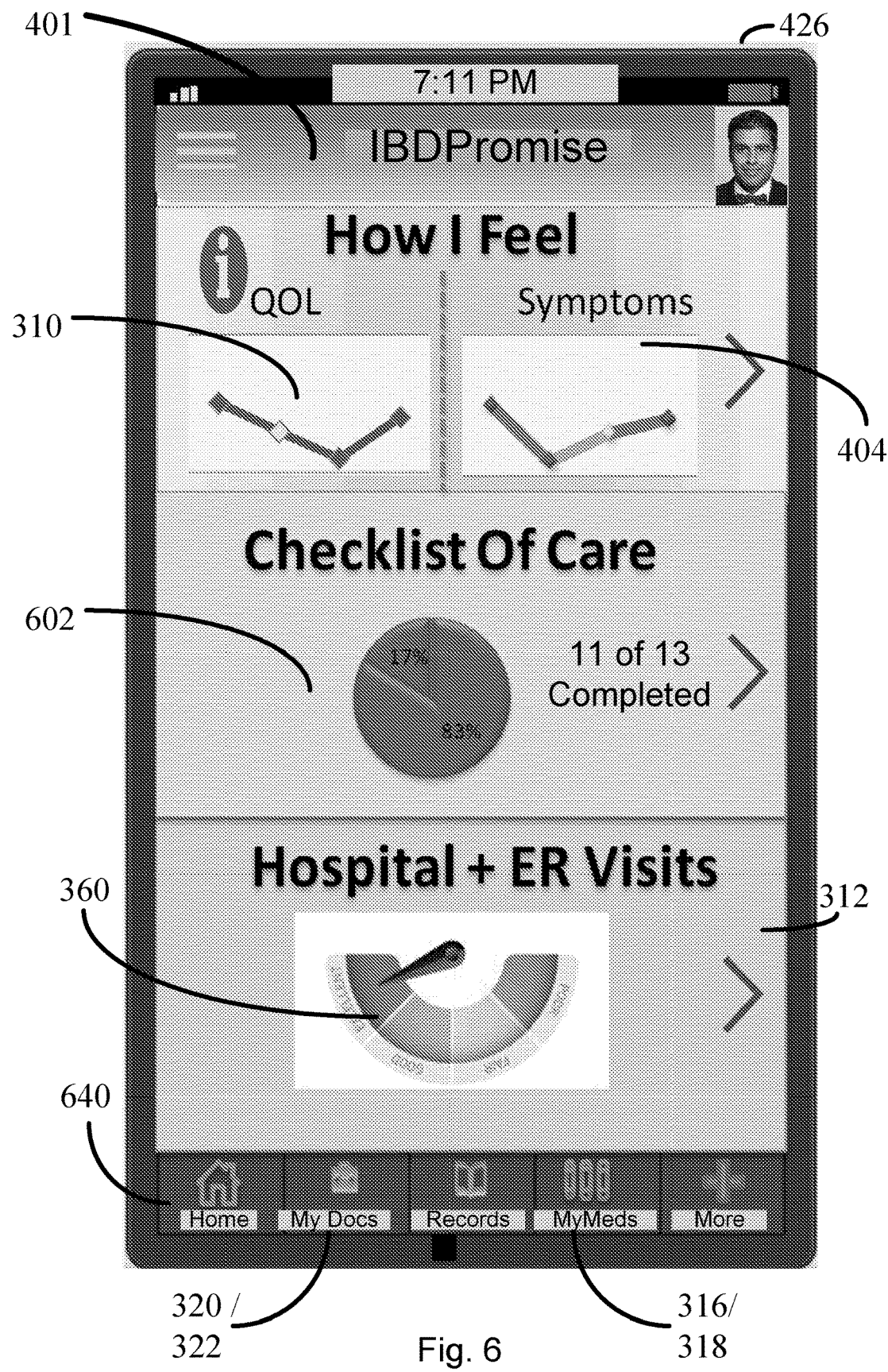
FIG. 6 illustrates an interface for a gastrointestinal indication monitoring application with a quality of life reporting panel in accordance with an aspect of the present disclosure.
Figure 14:
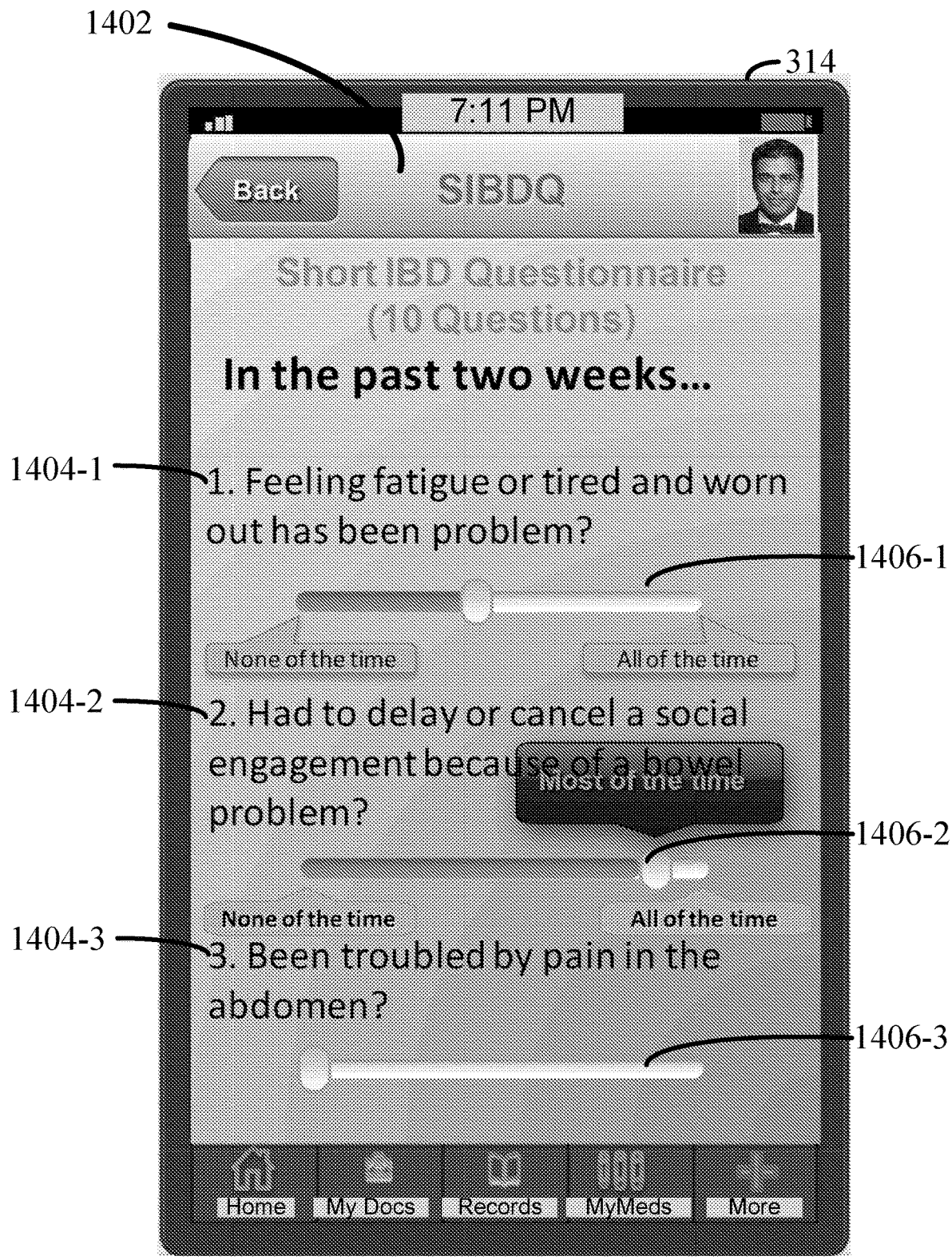
FIG. 14 illustrates a questionnaire input module within a gastrointestinal indication monitoring application in accordance with an aspect of the present disclosure.
Figure 15:
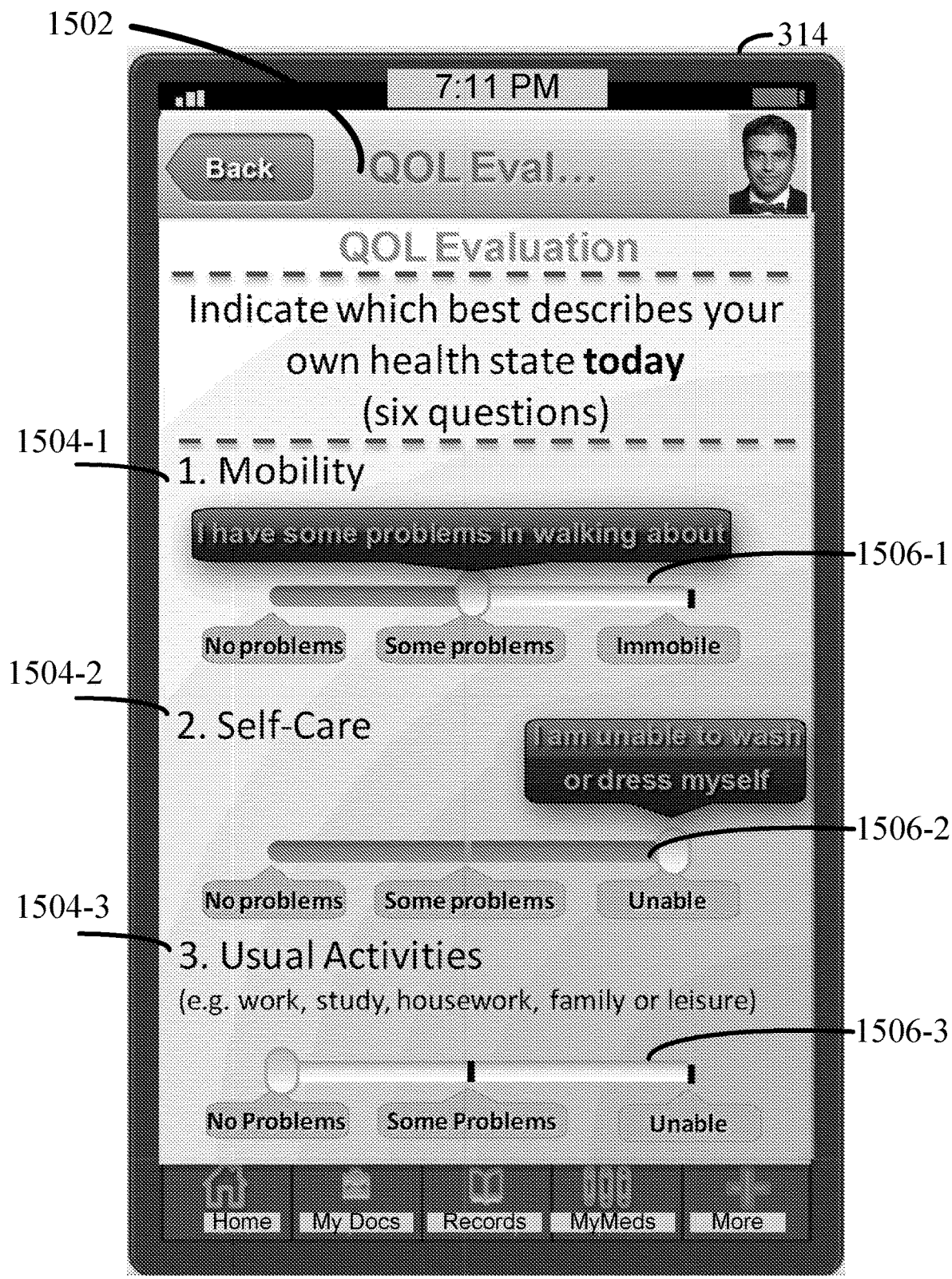
FIG. 15 illustrates another aspect of a questionnaire input module within a gastrointestinal indication monitoring application in accordance with an aspect of the present disclosure.

The device 102 further comprises a gastrointestinal indication monitoring module 426. FIG. 6 illustrates a gastrointestinal indication monitoring module 426 in accordance with an embodiment of the present disclosure. In some embodiments, the gastrointestinal indication monitoring module 426 provides, on a repeating basis over a period of time, a questionnaire regarding a plurality of conditions (e.g., via questionnaire input module 314). Each condition in the plurality of conditions arises, at least in part, from a chronic gastrointestinal indication associated with a subject. The questionnaire 1402 comprises a plurality of questions 1404. In some embodiments, each respective question in the plurality of questions (i) is associated with a corresponding condition in the plurality of conditions and (ii) comprises an affordance (e.g., a slide bar, an input field, a plurality of radio buttons, or a drop-down menu) that is configured to allow the subject to indicate a degree to which the subject presently associates with the corresponding condition. For instance, in some embodiments the affordance provides for the selection between a low value and a high value to allow the subject to indicate a degree to which the subject presently associates with the corresponding condition. In another example, the affordance provides different categorical possibilities to select (e.g. "always," "most of the time," "sometimes," "never"). For example, selection of item 404 of panel 401 of FIG. 6 leads, in some embodiments, to the questionnaire 1402 illustrated in FIG. 14 and/or questionnaire 1502 illustrated in FIG. 15. Referring to FIG. 14, the questionnaire 1402 comprises a plurality of questions 1404, and each respective question in the plurality of questions (i) is associated with a corresponding condition in a plurality of conditions (e.g., fatigue, cancellation of a social event, pain) and (ii) comprises an affordance (e.g., a slide bar 1406) that is configured to allow the subject to select between a low value and a high value to indicate a degree to which the subject presently associates with the corresponding condition. Referring to FIG. 15, the questionnaire 1502 comprises a plurality of questions 1504, and each respective question in the plurality of questions (i) is associated with a corresponding condition in a plurality of conditions (e.g., mobility, ability to self-care, ability to perform usual activities) and (ii) comprises an affordance (e.g., a slide bar 1506) that is configured to allow the subject to select between a low value and a high value to indicate a degree to which the subject presently associates with the corresponding condition. In some embodiments, not all of the questions in the plurality of questions is associated with a corresponding condition in the plurality of conditions.

In some embodiments, the gastrointestinal indication monitoring module 426 communicates with the chronic gastrointestinal indication tracking server 200 to, for example, obtain updates to the questionnaires, communicate the answers to the questionnaires and to share other medical information with the gastrointestinal indication tracking server (e.g., resource usage by the subject 216, subject medications/medication history, subject pharmacy, medical resources, and alerts).

In some embodiments, the gastrointestinal indication monitoring module 426 allows reporting of data captured automatically at device 102 (e.g., activity, sleep cycle, etc.). In some such embodiments, the gastrointestinal indication monitoring module 426 interfaces with other applications on the device 102 that collect such information. In some such embodiments, the gastrointestinal indication monitoring module 426 interfaces (e.g., by a wireless connection, such as Bluetooth, or by wire) with devices worn by the subject (e.g., wearable biometric devices) that collect such information. Examples of such wearable devices include, but are not limited to, JAWBONE, MISFIT, FITBIT, GARMIN, MICROSOFT BAND 2, MOOV NOW and equivalents, XIAOMI MI BAND and equivalents, SWAROVSKI SHINE and equivalents. Nonlimiting examples of such information that is collected by gastrointestinal indication monitoring module 426 in such embodiments are heart rate, sleep monitoring, daily step tracking, glucose detection, electrocephalograms, electrocardiograms, and electromyography.

Figure 12:
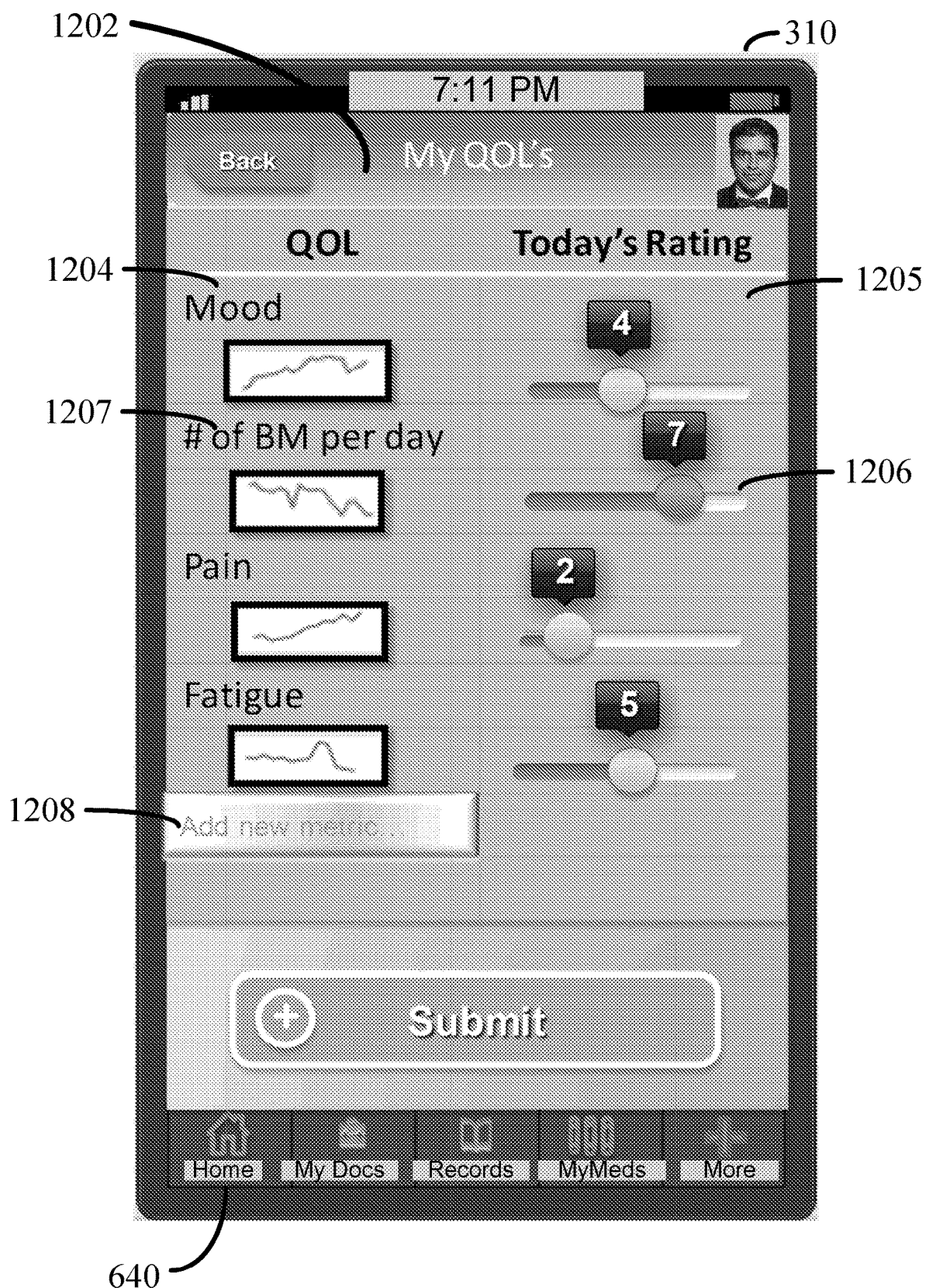
FIG. 12 illustrates a quality of life reporting panel in accordance with an aspect of the present disclosure.
Figure 13:
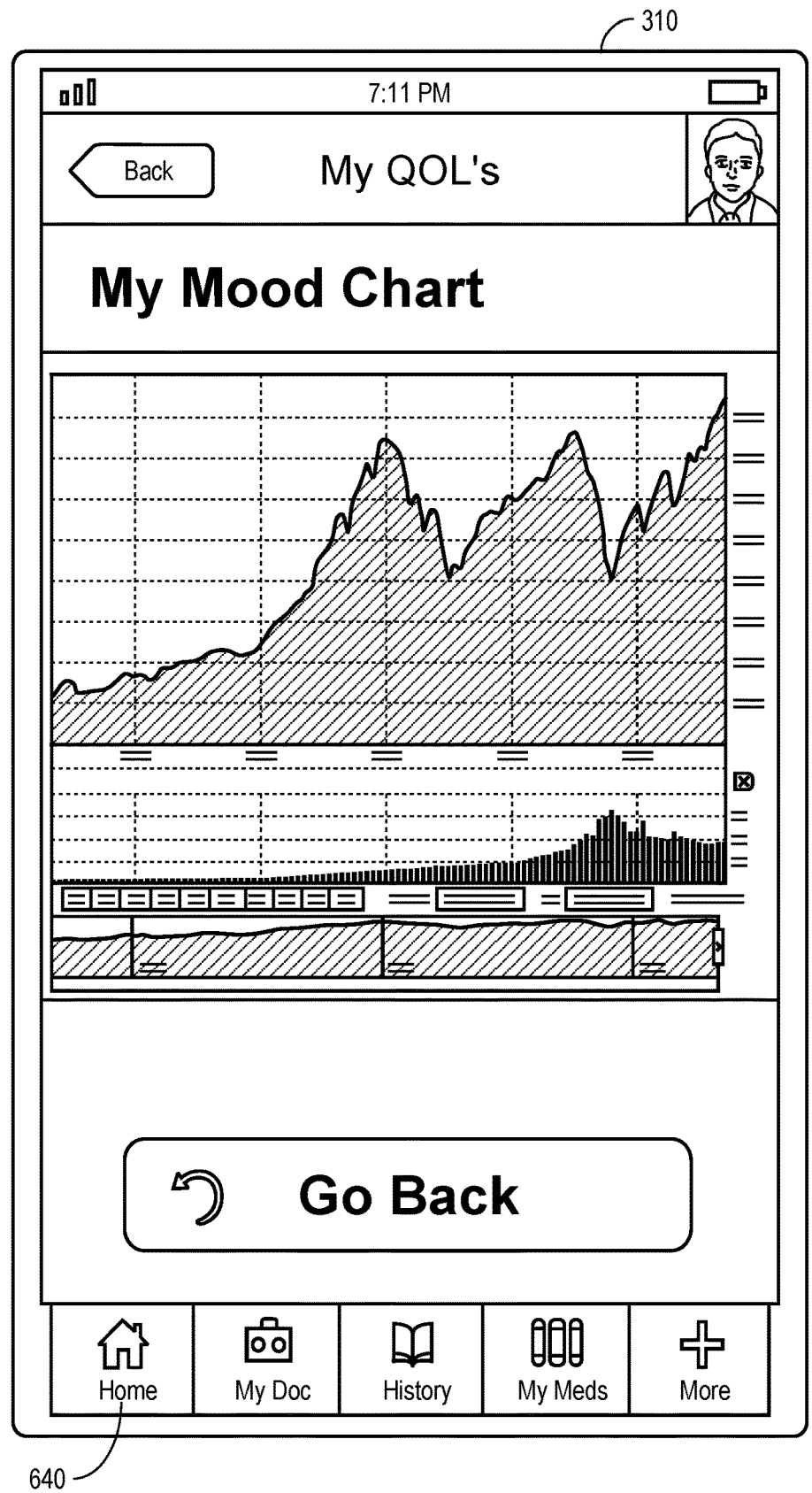
FIG. 13 illustrates another embodiment of a quality of life reporting panel in accordance with an aspect of the present disclosure.

Referring to FIGS. 3 and 6, in some embodiments, the gastrointestinal indication monitoring module 426 includes a quality of life reporting panel 310 that, responsive to a report request from the subject, provides a subject report comprising a graphical quality of life measure of the subject as a function of time based upon answers to a plurality of questions in a questionnaire over a period of time. In some embodiments, the graphical quality of life measure incorporates (i) a subjective assessment, made by the subject, of a social factor affected by the chronic gastrointestinal indication and (ii) an objective assessment of an illness factor associated with the gastrointestinal indication. In some embodiments, this objective assessment is provided by the subject (e.g., number of bowel movements). FIG. 12 illustrates in further detail. When a subject selects quality of life 310 of panel 401 in FIG. 6, quality of life panel 1202 of FIG. 12 is displayed in some embodiments which shows (i) a subjective assessment 1205, made by the subject, of a social factor (e.g., mood 1204) affected by the chronic gastrointestinal indication and (ii) an objective assessment 1206 of an illness factor (e.g., number of bowel movements per day 1207) associated with the gastrointestinal indication. In the embodiment illustrated in FIG. 12, a rating for each of several such metrics (social factors or illness factors) associated with the gastrointestinal indication is provided. Examples of such metrics include pain and fatigue. Furthermore, the subject is given the option to provide additional metrics affected by the chronic gastrointestinal indication 1208. Selection of a metric (e.g. mood 1204) from panel 1202 leads to more detailed information regarding the metric, as illustrated in panel 1302 of FIG. 13. In FIG. 13, the score for this metric as a function of time is plotted.

Figure 7:
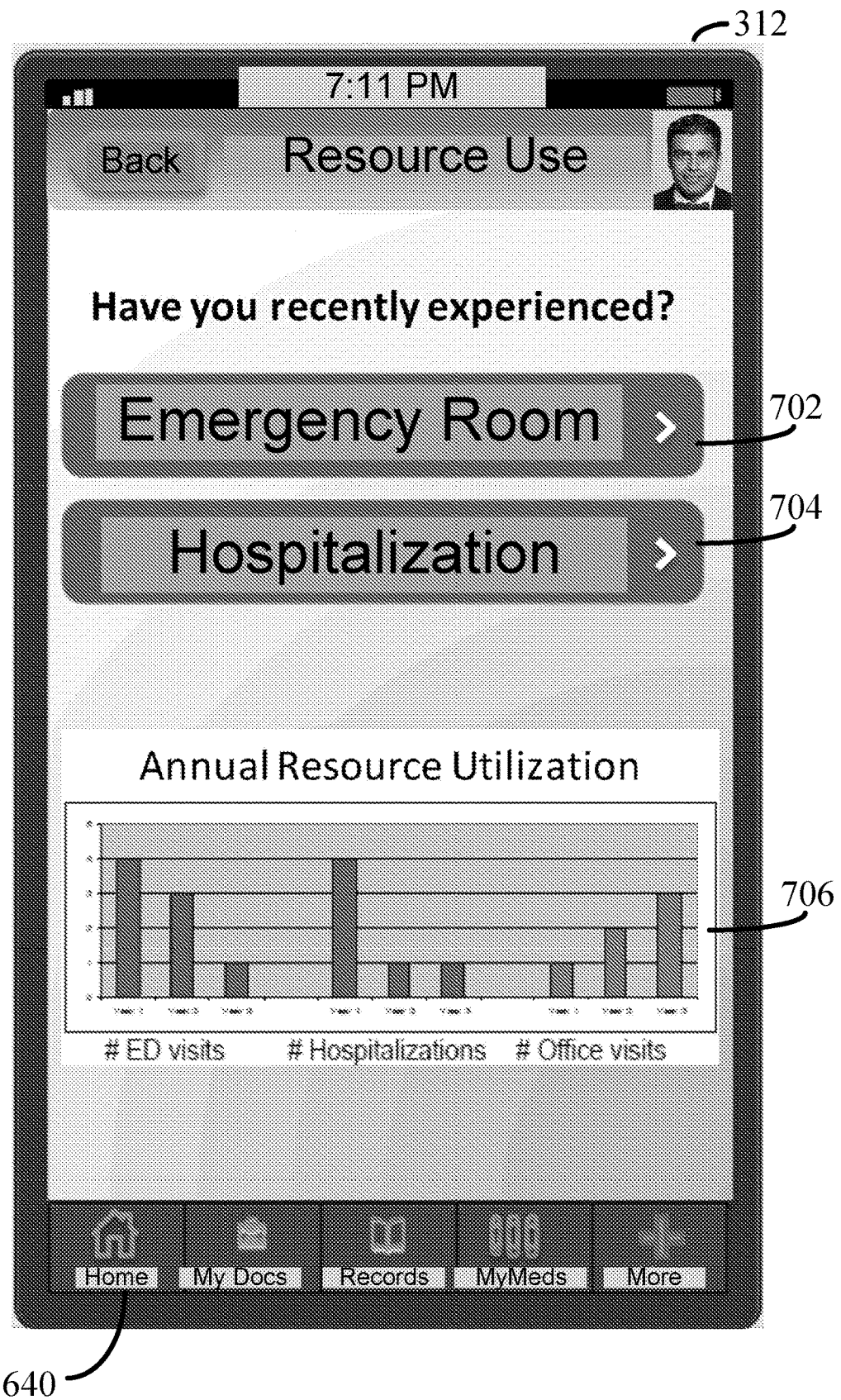
FIG. 7 illustrates a resource use module within a gastrointestinal indication monitoring application in accordance with an aspect of the present disclosure.
Figure 8:
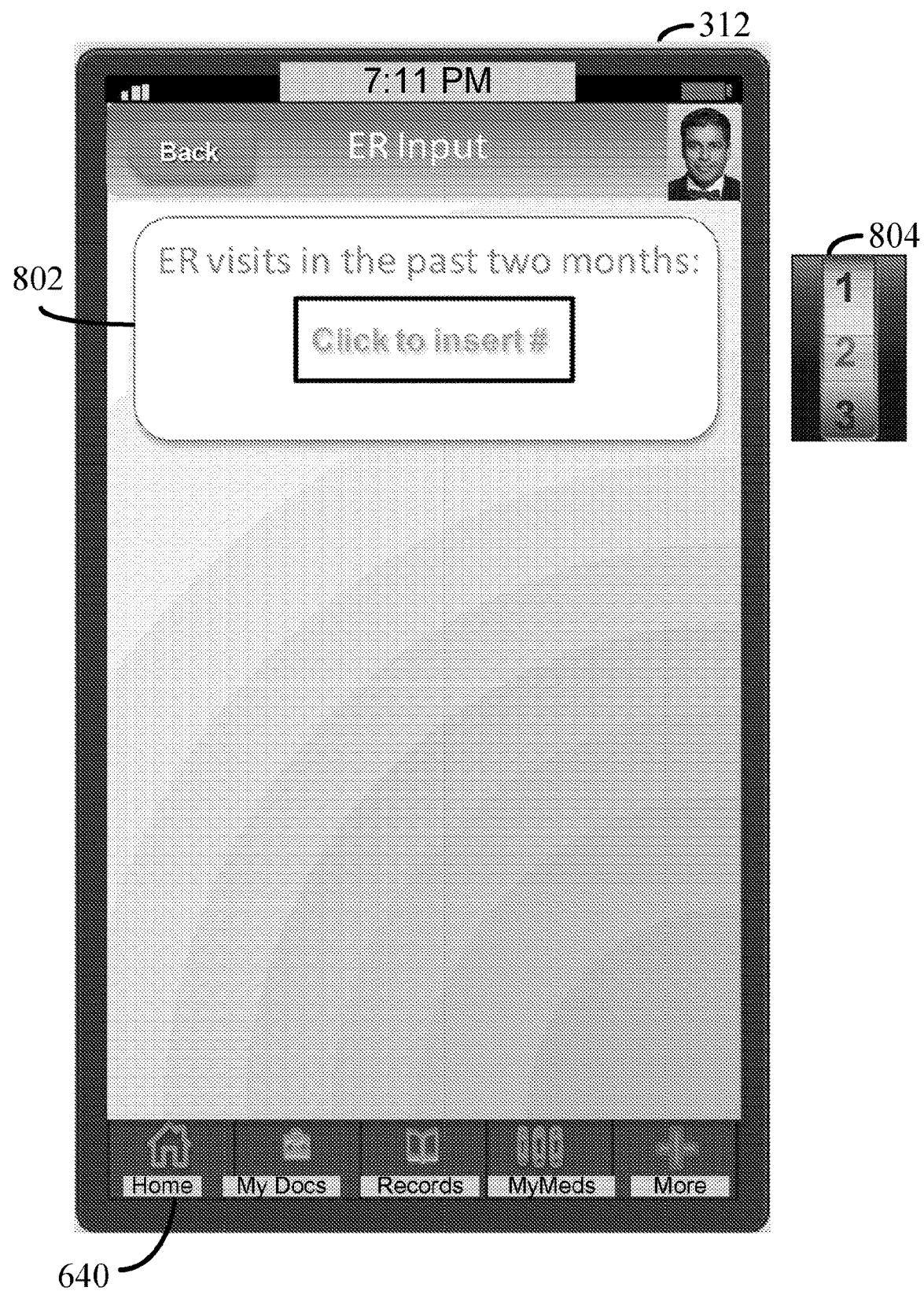
FIG. 8 illustrates a subject input screen for a resource use module within a gastrointestinal indication monitoring application in accordance with an aspect of the present disclosure.
Figure 9:
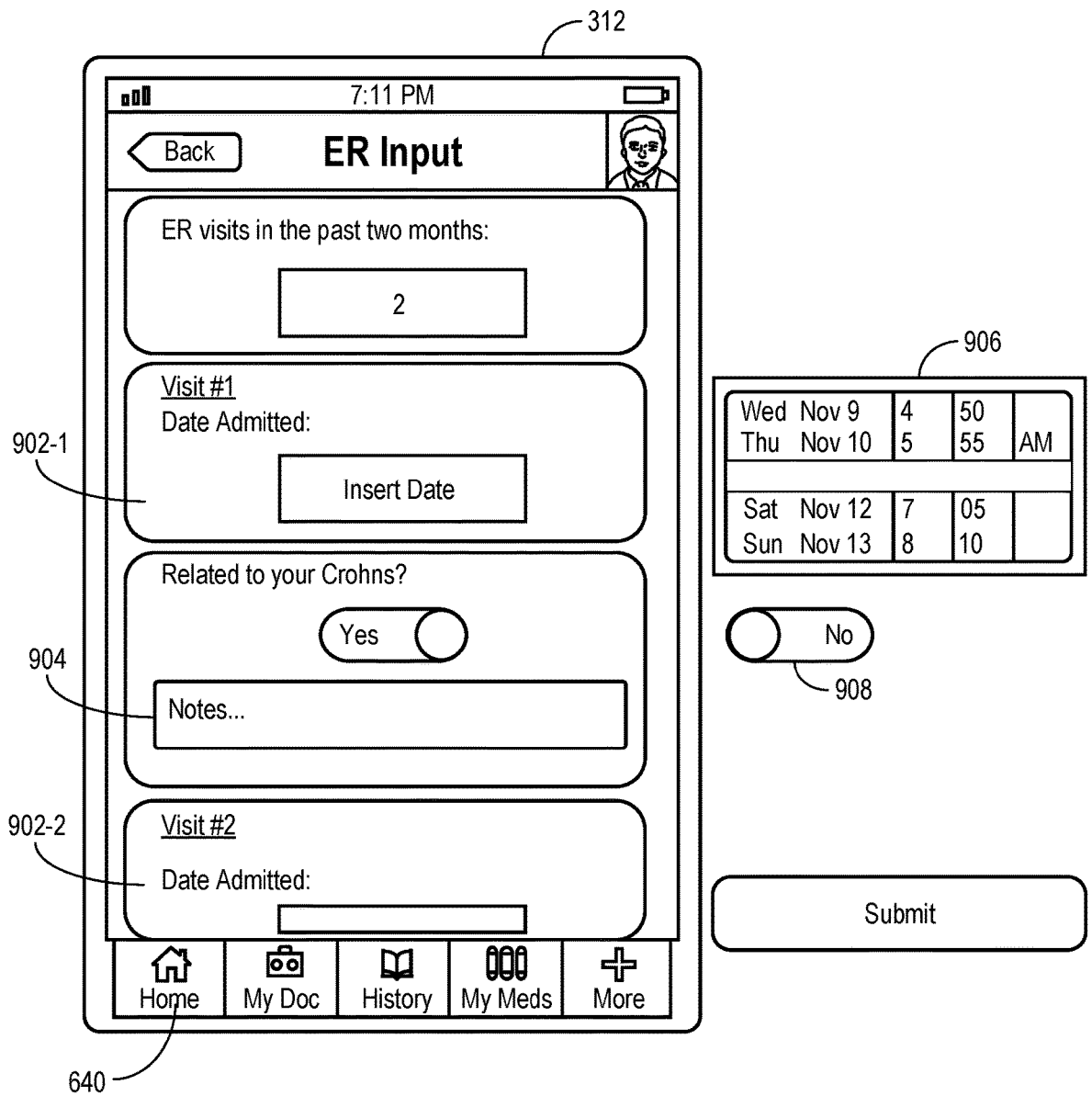
FIG. 9 illustrates another subject input screen for a resource use module within a gastrointestinal indication monitoring application in accordance with an aspect of the present disclosure.

Referring to FIGS. 3 and 6, in some embodiments, the gastrointestinal indication monitoring module 426 includes a resource use module 312 that tracks utilization of the subject 216 of one or more resources. In some embodiments, the resource use module 312 includes an input mechanism for inputting usage by the subject 216 of resources (e.g., emergency room visits and hospitalization visits) in the one or more resources, and a plotting mechanism that plots usage of the one or more resources by the subject over a period of time. FIGS. 7 through 9 illustrate different examples of resource use module 312. Referring to FIG. 7, the subject is provided with the option to enter an emergency room 702, hospitalization 704, or office visit event data. Usage of such resources in past years is also shown in graph format (e.g., bar graph) 706. Referring to FIG. 8, upon selection of emergency room toggle 702 of FIG. 7, the subject is provided the option to enter the number of emergency room visits in the past predetermined period of time (e.g., the past two months) 802. In some embodiments, the subject enters a responsive number using a keyboard. In some embodiments, the subject provides a responsive number using an input interface such as number picker 804. Referring to FIG. 9, when the subject indicates that there has been an emergency room visit, further questions are provided to determine whether the emergency room visit was for the chronic gastrointestinal indication as well as to find out other information about the visit. For instance, the subject is asked about the admission date 902, and whether the visit was related to the chronic gastrointestinal indication (e.g., Crohn's disease) 904. In some embodiments, the subject enters such information using a slide bar, an input field, a plurality of radio buttons, and/or a drop-down menu). In FIG. 9, an example of a date picker 906 that can be used to provide the admission date 902 is illustrated. Also in FIG. 9, an example of a slide bar 908 that can be used to indicate whether the visit was related to the chronic gastrointestinal indication 906 is illustrated.

Figure 10:
FIG. 10 illustrates still another subject input screen for a resource use module within a gastrointestinal indication monitoring application in accordance with an aspect of the present disclosure.
Figure 11:
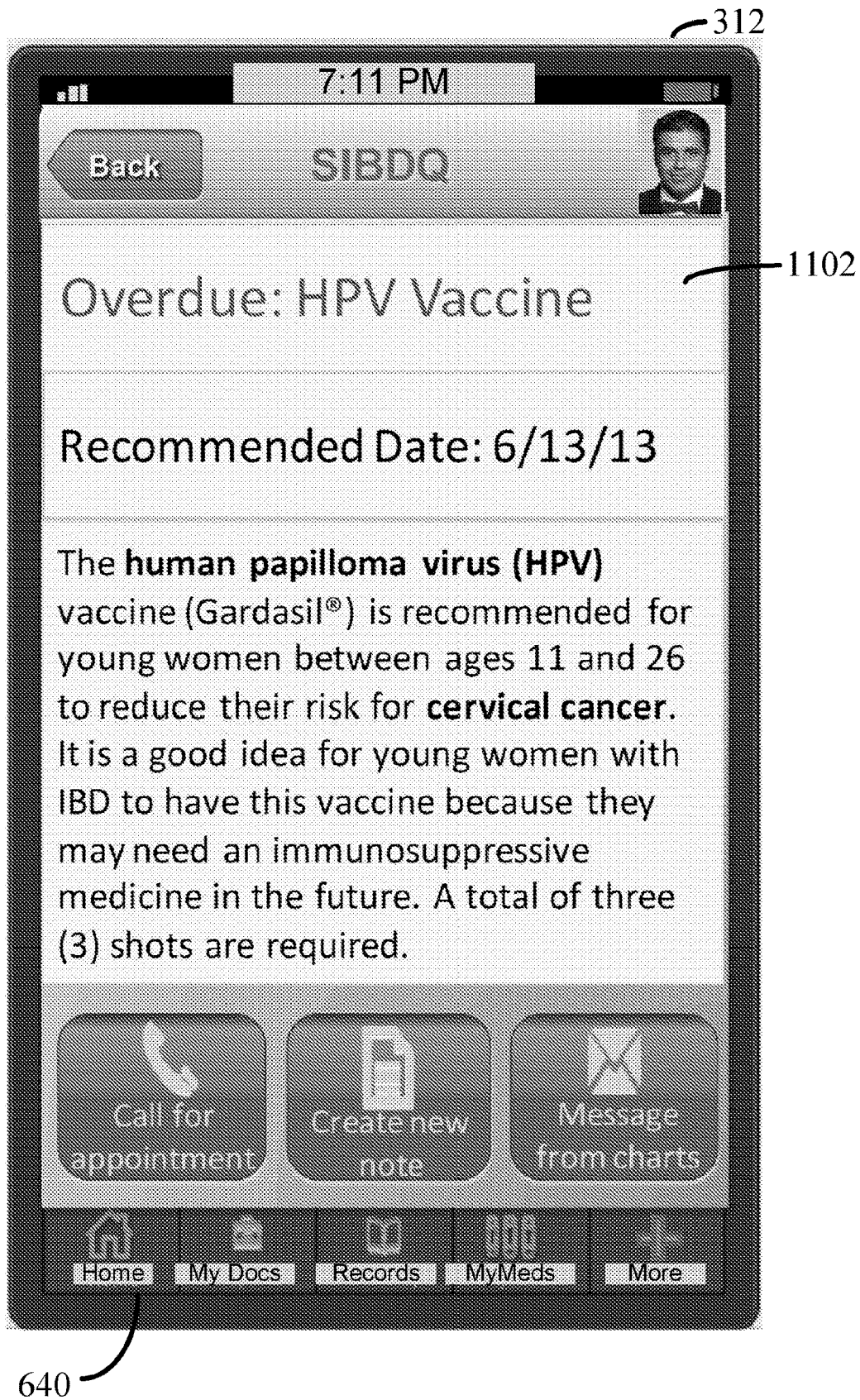
FIG. 11 illustrates another screen of a resource use module within a gastrointestinal indication monitoring application in accordance with an aspect of the present disclosure.

Referring to FIGS. 6 and 10, the gastrointestinal indication monitoring module 426 further provides a checklist of care 602 module. Referring to FIG. 10, activation of this module leads to a panel 1002 in which the subject is advised of which interventions the subject has not accomplished 1002 and which interventions the subject has accomplished 1004. For instance, still referring to FIG. 10, examples of interventions include vaccination 1004, bone density test 1006, mucosal healing 1006 and annual colonoscopy 1008. Moreover, the subject can search for interventions using search interface 1012. Selection of any of these interventions in panel 1001 leads to more information regarding an intervention. For example, selection of vaccination 1004 of FIG. 10 leads to panel 1102 of FIG. 11 in which more information regarding vaccinations is provided.

Referring to FIGS. 3, 6 and 16 and 26, in some embodiments, the gastrointestinal indication monitoring module 426 includes a medications/medication history module 316 that tracks one or more medicines that the subject 216 is taking to alleviate the chronic gastrointestinal indication. For instance, in some embodiments, selecting affordance 316 of panel 401 of FIG. 6 leads to panel 1602 of FIG. 16 which provides ways for the subject to track medications the subject 216 is taking to alleviate the chronic gastrointestinal indication. As an example, affordance 1604 enables the subject to add new medications, affordance 1606 allows the subject to peruse current medications, and affordance 1608 allows the subject to review past medications taken for the chronic gastrointestinal indication.

Figure 16:
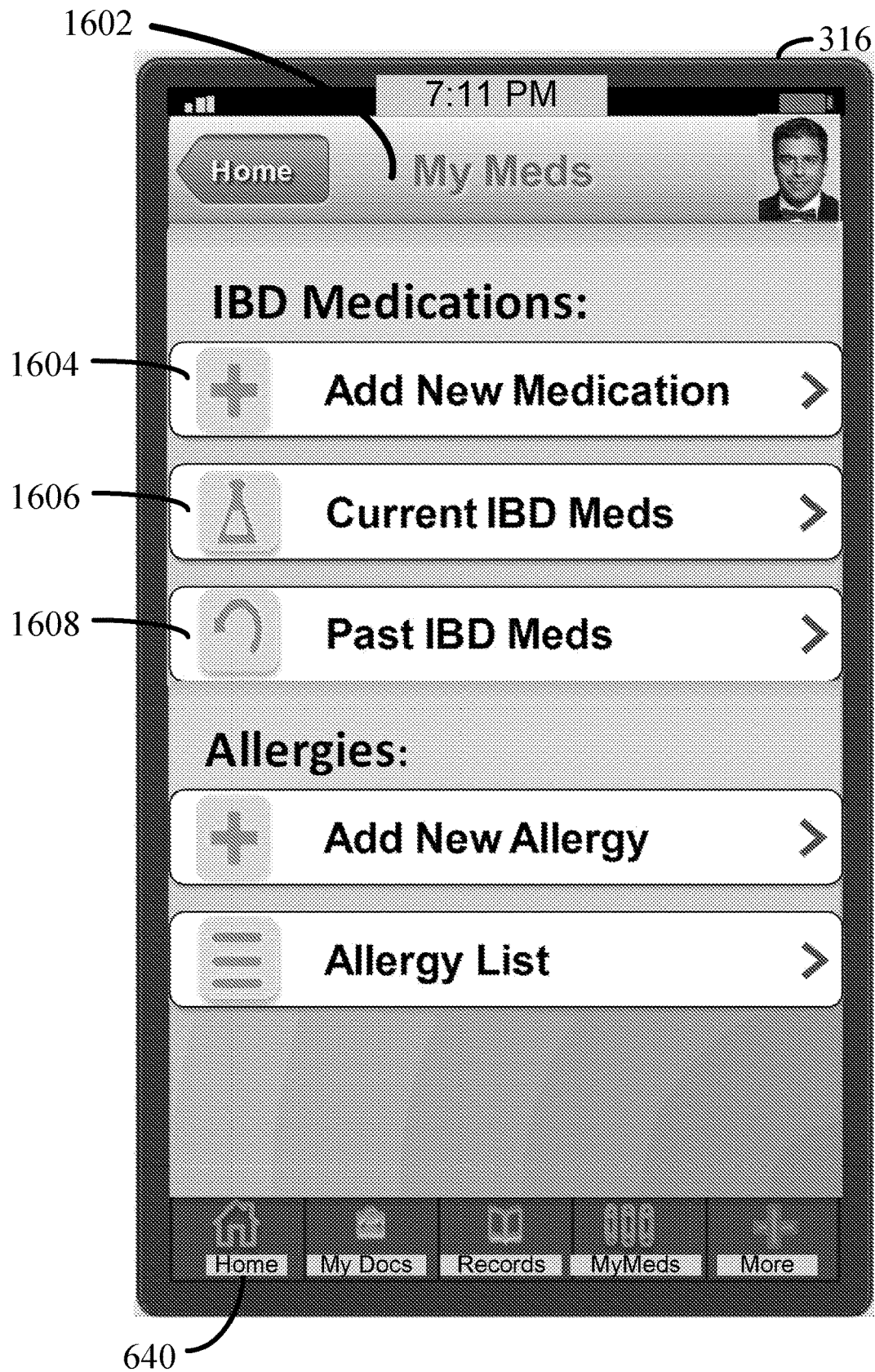
FIG. 16 illustrates a panel of a medications/medication history module within a gastrointestinal indication monitoring application in accordance with an aspect of the present disclosure.
Figure 17:
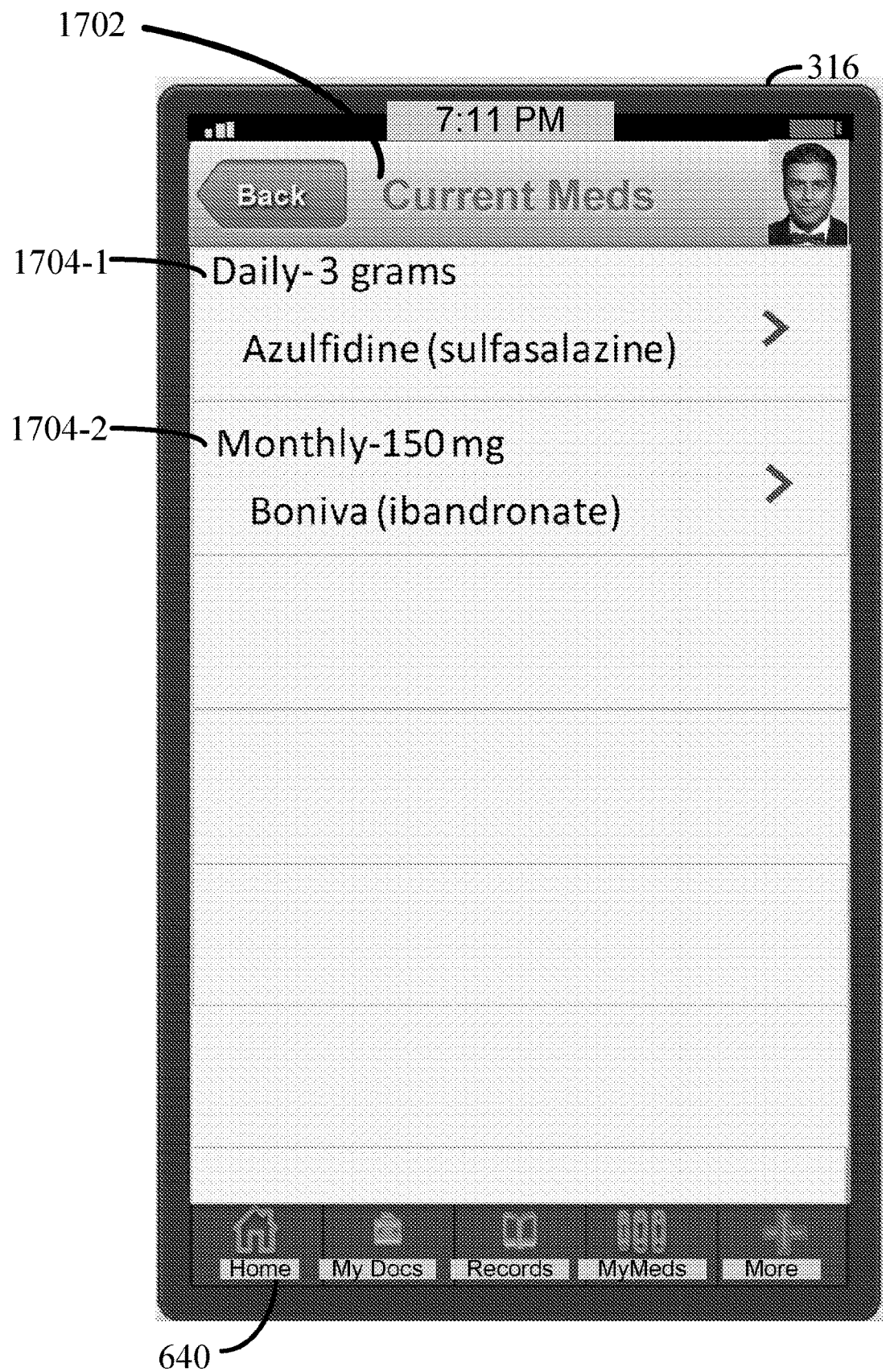
FIG. 17 illustrates another panel of a medications/medication history module within a gastrointestinal indication monitoring application in accordance with an aspect of the present disclosure.
Figure 18:
FIG. 18 illustrates another panel of a medications/medication history module within a gastrointestinal indication monitoring application in accordance with an aspect of the present disclosure.

In more detail, selection of affordance 1606 of FIG. 16 brings up panel 1702 of FIG. 17, in some embodiments, where current medications 1704 are provided. Advantageously, further still, selection of a medication 1704 from panel 1702 brings up panel 1802 of FIG. 18, in some embodiments, in which more details of the medication 1704 are provided, including dosage and unit 1804, frequency of administration 1806, and additional notes 1808.

Figure 19:
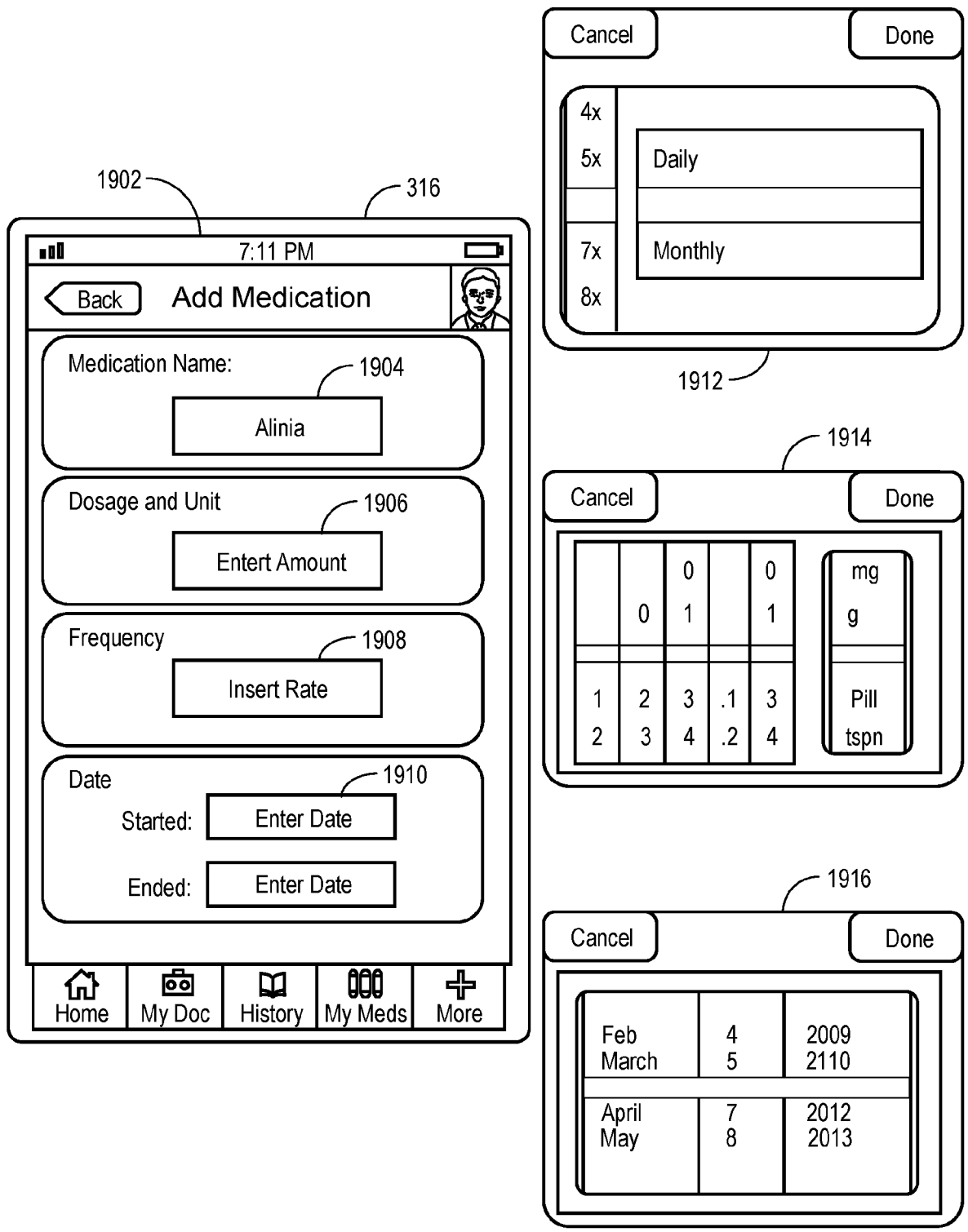
FIG. 19 illustrates another panel of a medications/medication history module within a gastrointestinal indication monitoring application in accordance with an aspect of the present disclosure in which a subject in prompted to enter information about a new medication the subject is taking.

Selection of affordance 1604 of FIG. 16 brings up panel 1902 of FIG. 19, in some embodiments, where an interface for adding new medication is provided that includes affordances for entering the medication name 1904, dosage and unit 1906, frequency 1908, and start and end dates 1910. For instance, in some embodiments, frequency 1908 is identified using picker 192, dosage and unit 1906 is identified using picker 194, and start date and end date 1910 are identified using instances of picker 1916.

Advantageously, referring to panels 2902, 3002, 3102, and 3202 of FIGS. 29 through 32, medications/medication history module 316 not only stores information regarding the medications the subject is supposed to take, in some embodiments, the module also queries the subject as to whether they are actually taking the medications.

Figure 26:
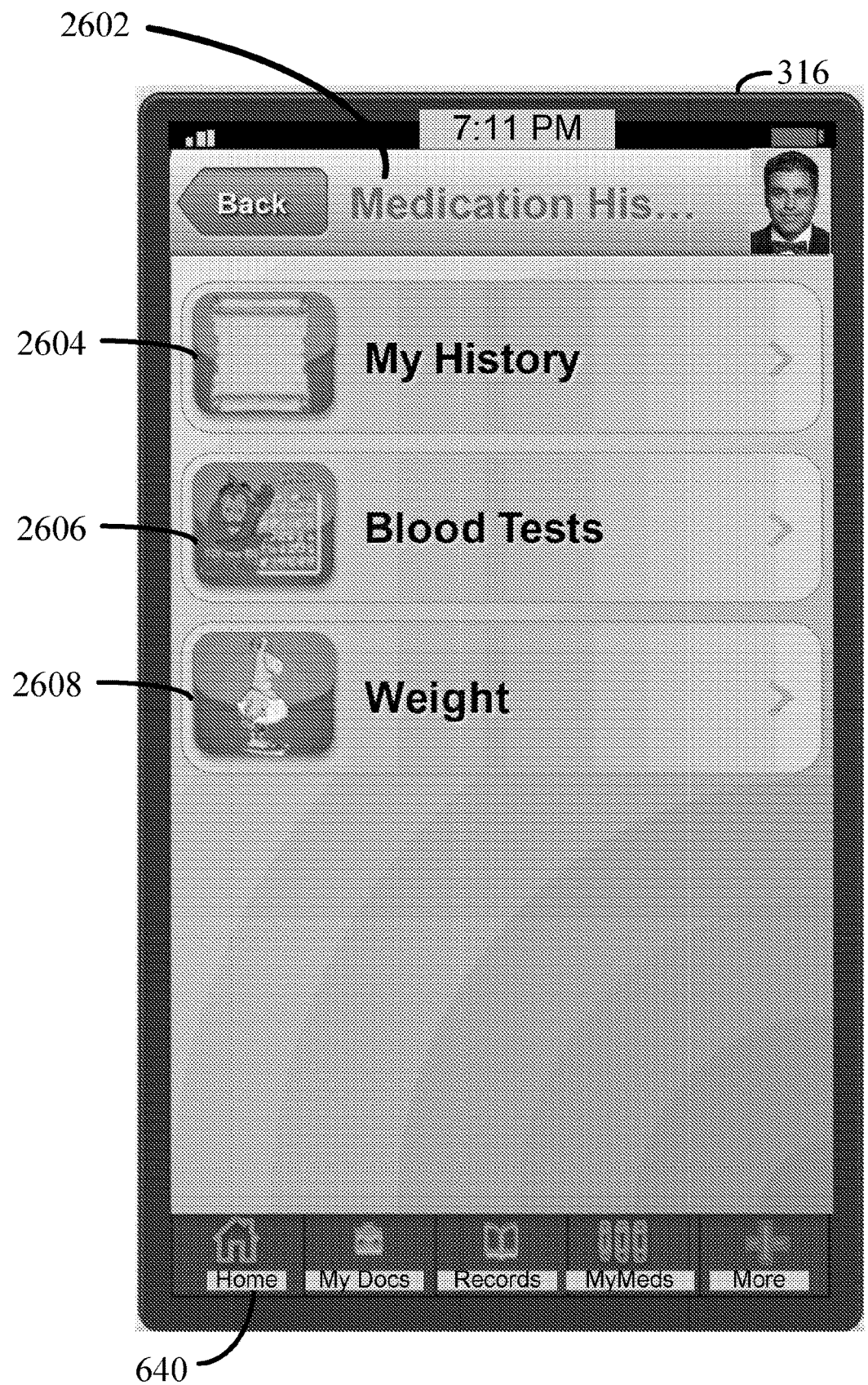
FIG. 26 illustrates a panel of a medications/medication history module within a gastrointestinal indication monitoring application in accordance with an aspect of the present disclosure.
Figure 27:
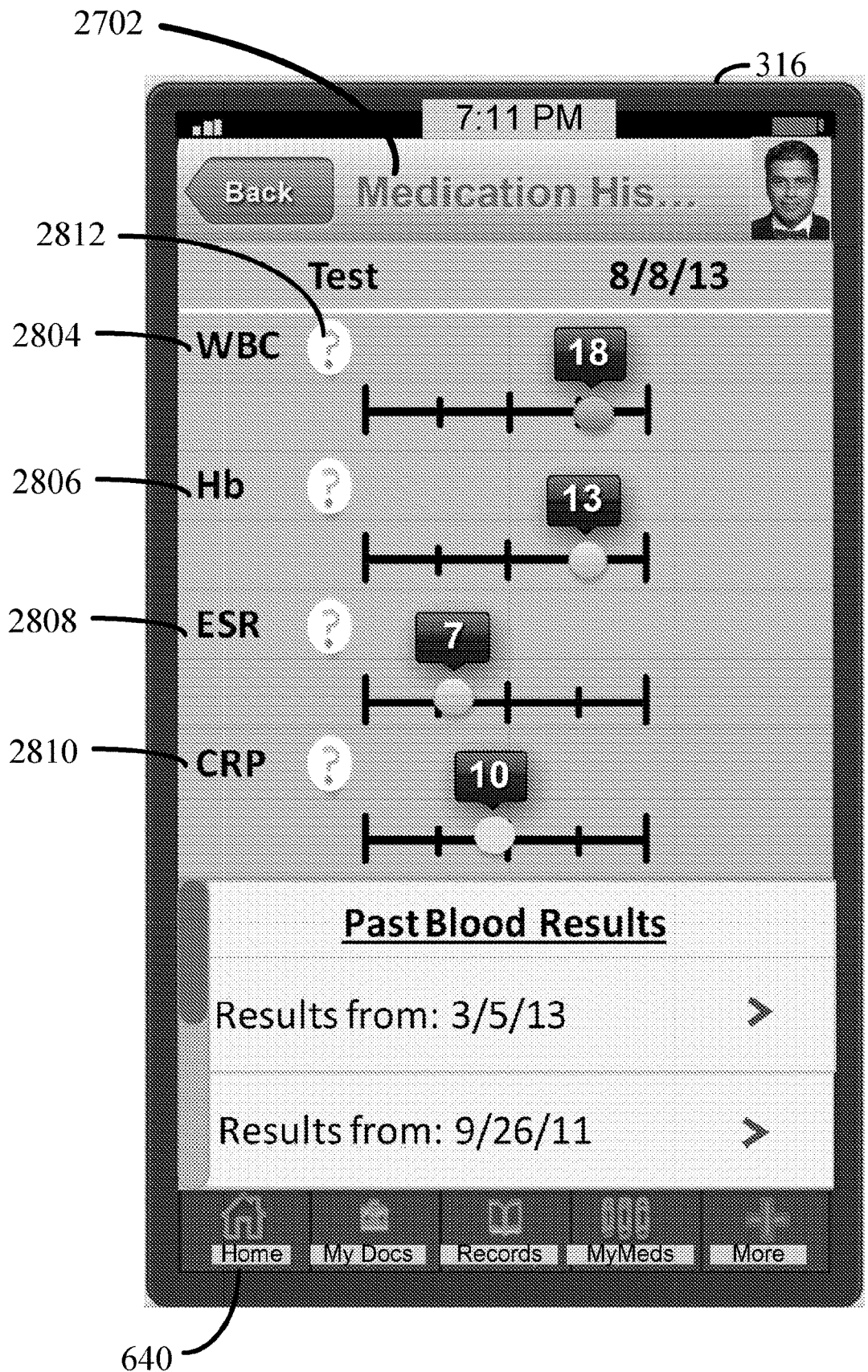
FIG. 27 illustrates another panel of a medications/medication history module within a gastrointestinal indication monitoring application in accordance with an aspect of the present disclosure.
Figure 28:
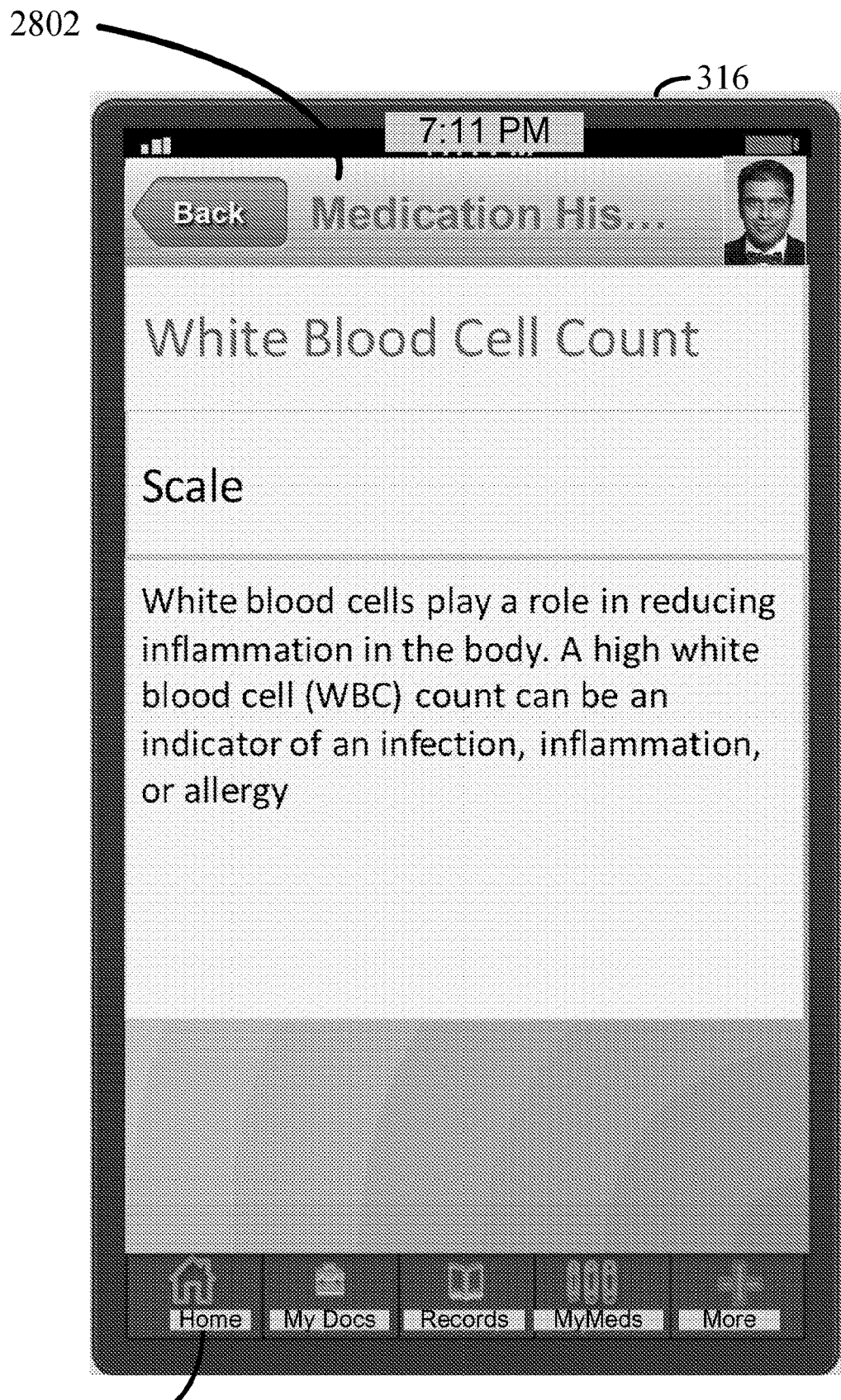
FIG. 28 illustrates another panel of a medications/medication history module within a gastrointestinal indication monitoring application in accordance with an aspect of the present disclosure.
Figure 29:
FIG. 29 illustrates another panel of a medications/medication history module within a gastrointestinal indication monitoring application in accordance with an aspect of the present disclosure.
Figure 30:
FIG. 30 illustrates another panel of a medications/medication history module within a gastrointestinal indication monitoring application in accordance with an aspect of the present disclosure.
Figure 31:
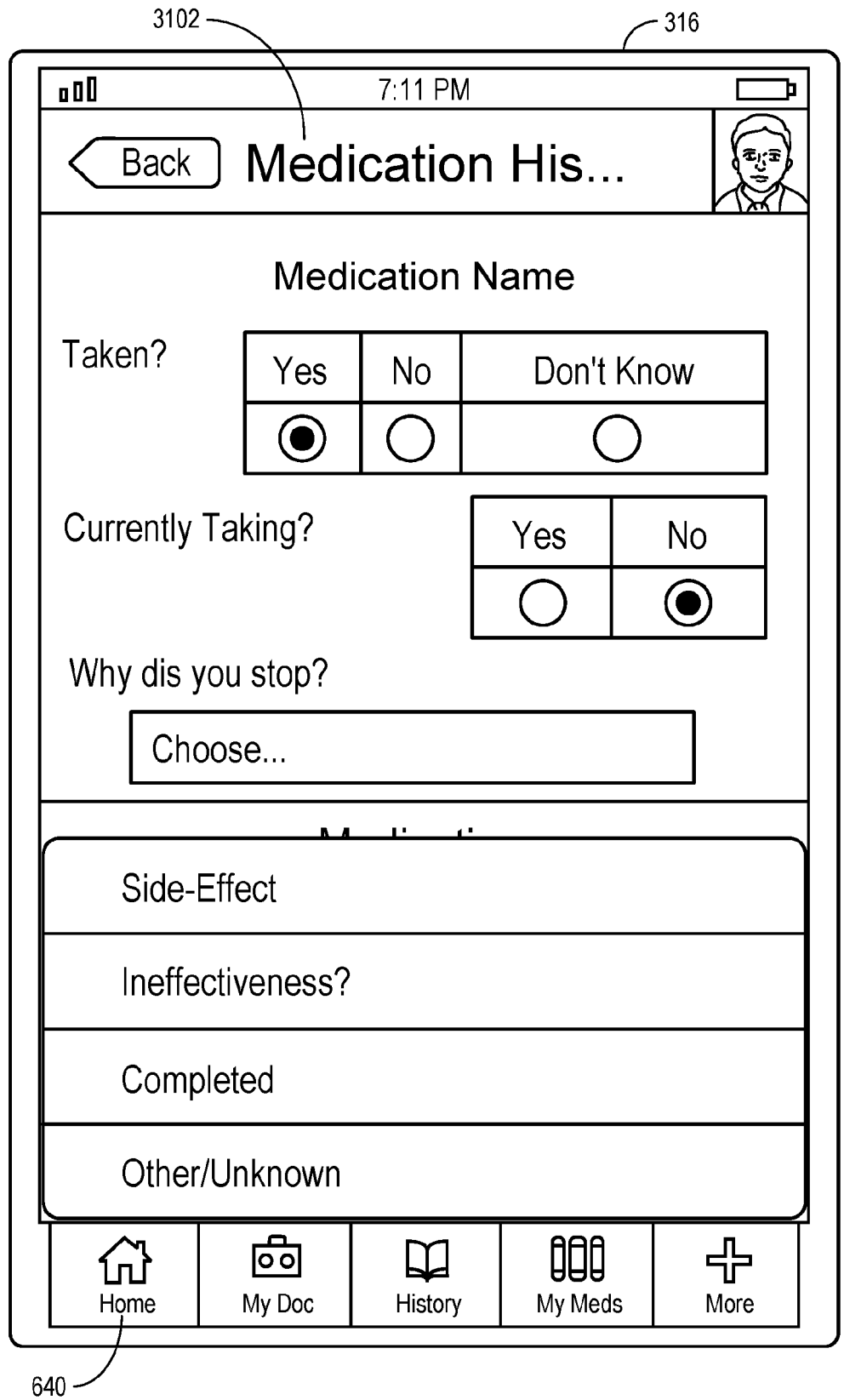
FIG. 31 illustrates another panel of a medications/medication history module within a gastrointestinal indication monitoring application in accordance with an aspect of the present disclosure.
Figure 32:
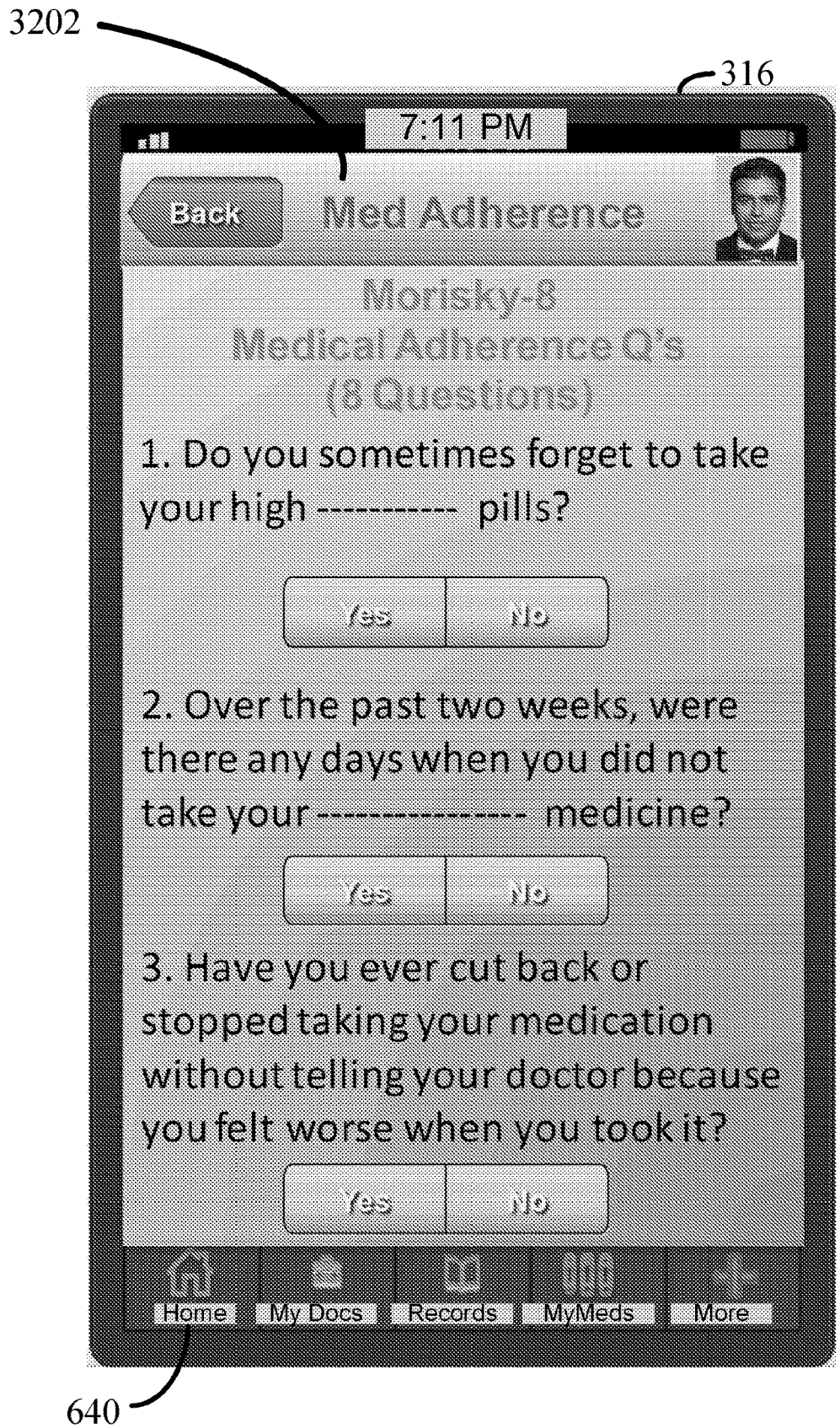
FIG. 32 illustrates another panel of a medications/medication history module within a gastrointestinal indication monitoring application in accordance with an aspect of the present disclosure.

In some embodiments, referring to FIG. 26, the subject 216 is further provided with a panel 2602 that provides the subject with their medical history 2604, blood tests 2606 and weight 2608. Selection of blood test affordance 2606 of FIG. 26 yields panel 2702 of FIG. 27 which details blood test results, including white blood cell count (WBC) 2804, haemoglobin (Hb) count 2806, erythrocyte sedimentation rate (ESR) 2808, C-reactive protein (CRP) 2810, plasma viscosity (not shown), and neutrophil count (not shown). By selection of an information toggle associated with any of these test results, further information is provided about the test. For instance, selection of the information toggle 2812 associated with WBC 2804 leads to panel 2802 of FIG. 28, in some embodiments, in which further information regarding this test is provided.

Figure 20:
FIG. 20 illustrates a panel of an allergies module within a gastrointestinal indication monitoring application in accordance with an aspect of the present disclosure.
Figure 21:
FIG. 21 illustrates another panel of an allergies module within a gastrointestinal indication monitoring application in accordance with an aspect of the present disclosure.

Referring to FIGS. 3, 6 and 20, in some embodiments, the gastrointestinal indication monitoring module 426 includes an allergies module 318 that tracks the allergies of the subject 216. In some embodiments, the allergies module 318 comprises an input mechanism for inputting allergies by the subject. For instance, selecting affordance 318 of panel 401 of FIG. 6 leads to panel 2002 of FIG. 20, in some embodiments, which provides ways for the subject to indicate which medications 2004 the subject is allergic to. In turn, selecting a medication 2004 in panel 2002 leads to a corresponding panel 2102, in some embodiments, illustrated in FIG. 21, in which further information regarding the allergy is provided, such as the date first noticed 2104 and the symptoms that arose 2106.

Figure 22:
FIG. 22 illustrates a panel of a medical practitioner caretaker module within a gastrointestinal indication monitoring application in accordance with an aspect of the present disclosure.

Referring to FIGS. 3, 6 and 22, in some embodiments, the gastrointestinal indication monitoring module 426 includes a medical practitioner caretaker module 320 that tracks contact information for medical practitioner caretakers associated with the subject 216. In some embodiments, the medical practitioner caretaker module 320 comprises an input mechanism for inputting medical practitioner caretaker information by the subject 216. For example, by selection of the affordance 320 for the medical practitioner caretaker module 320 of FIG. 6, panel 2202 of FIG. 22 is displayed in some embodiments. Here, the subject is provided with affordances for their primary physician 2204, gastroenterologist 2206, and pharmacy 2208. Further, the subject is provided with affordances for adding new notes 2210 or reviewing past notes from prior doctor visits 2212. By selecting the home key 640, the subject is returned to panel 401 of FIG. 6.

Figure 23:
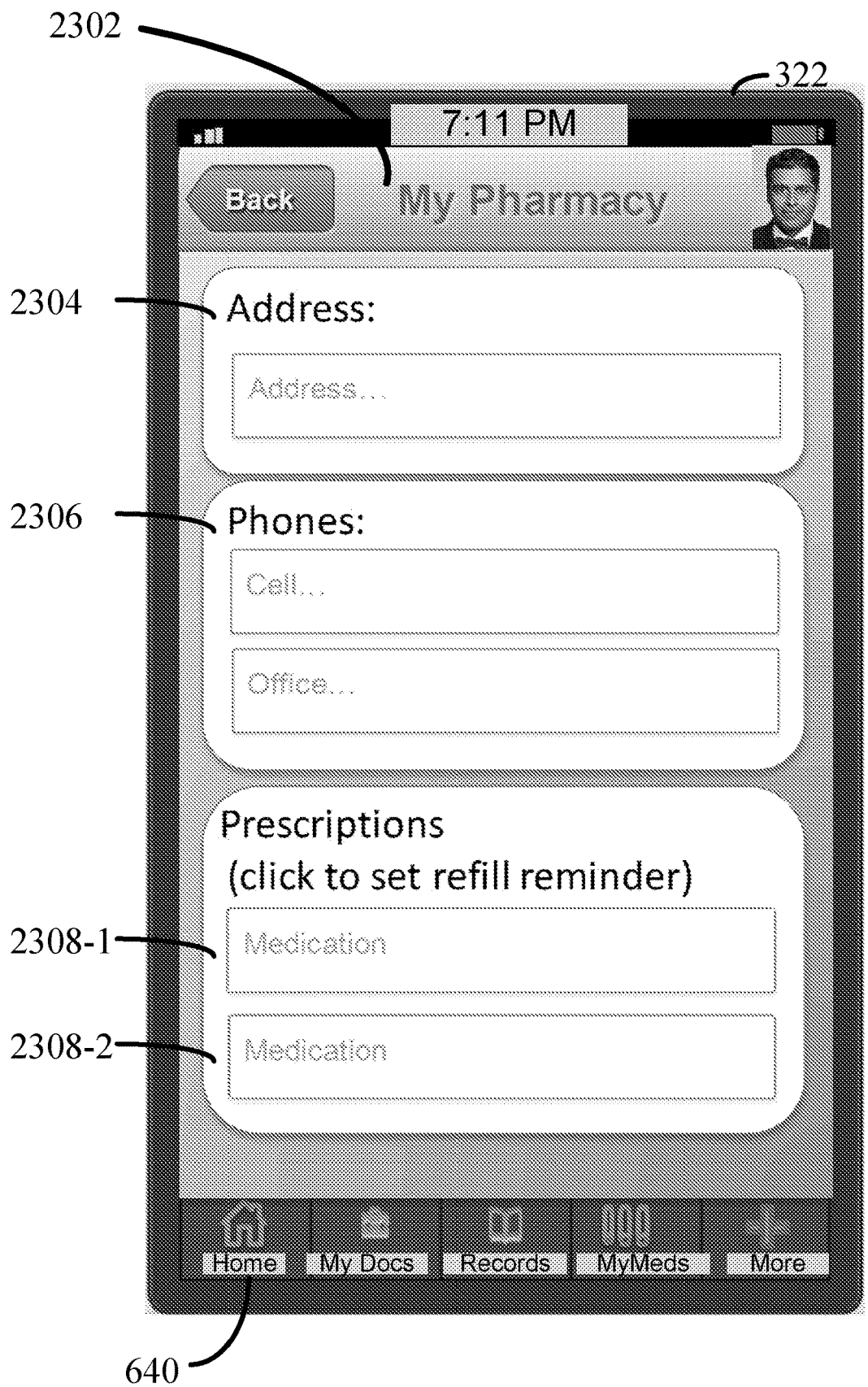
FIG. 23 illustrates a panel of a pharmacy module within a gastrointestinal indication monitoring application in accordance with an aspect of the present disclosure.

Referring to FIGS. 3, 6 and 23, in some embodiments, the gastrointestinal indication monitoring module 426 includes a pharmacy module 322 that tracks contact information for one or more pharmacies associated with the subject 216. In some embodiments, the pharmacy module 322 comprises an input mechanism for inputting pharmacy information by the subject 216. For example, by selection of the affordance 322 for the medical practitioner caretaker module 322 of FIG. 6, panel 2302 of FIG. 23 is displayed in some embodiments. Here, the subject is provided with affordances for entering pharmacy information, such as address 2304, and phone number 2306, and prescriptions 2308. By selecting the home key 640, the subject is returned to panel 401 of FIG. 6.

Figure 24:
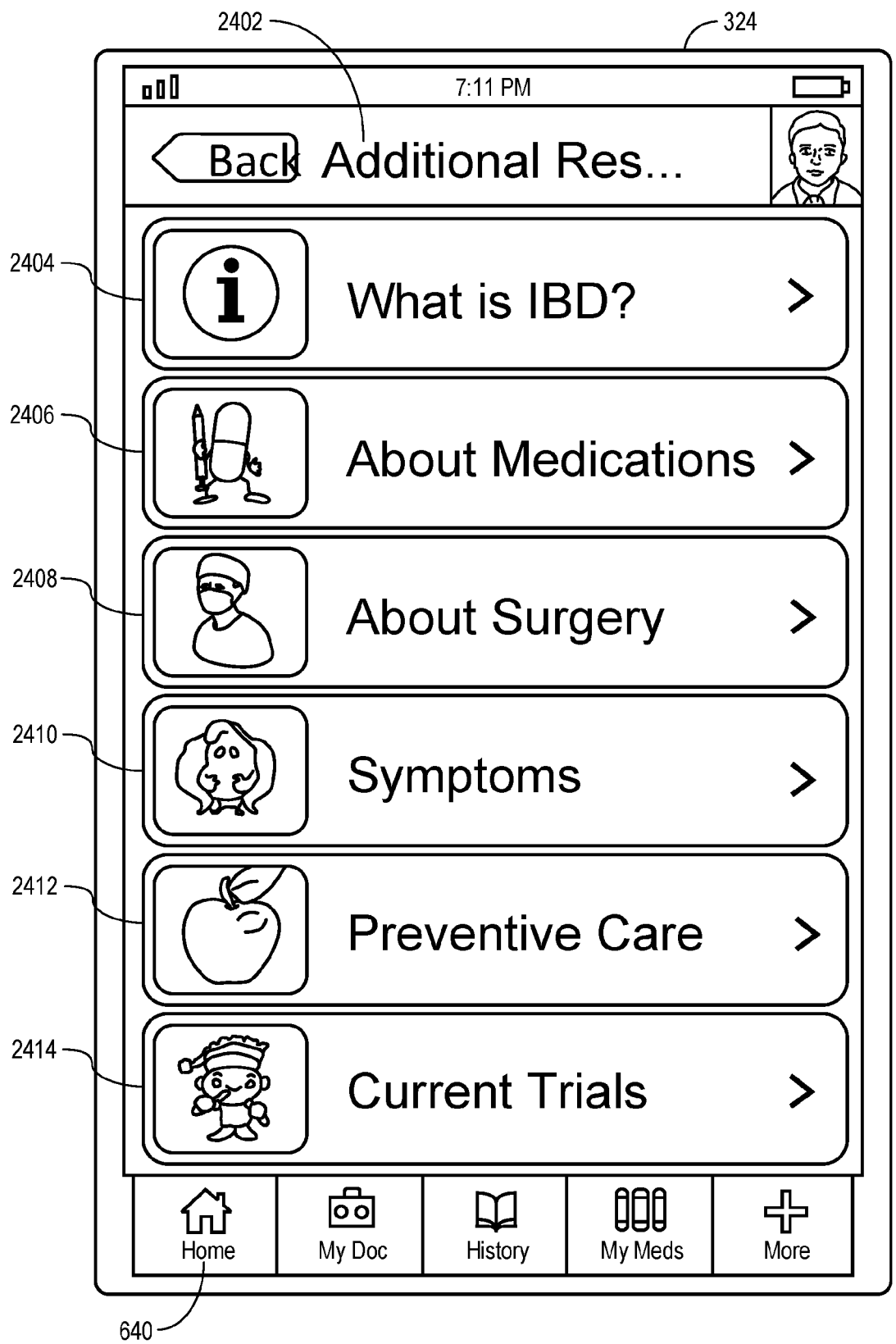
FIG. 24 illustrates a panel of a medical resource module within a gastrointestinal indication monitoring application in accordance with an aspect of the present disclosure.
Figure 25:
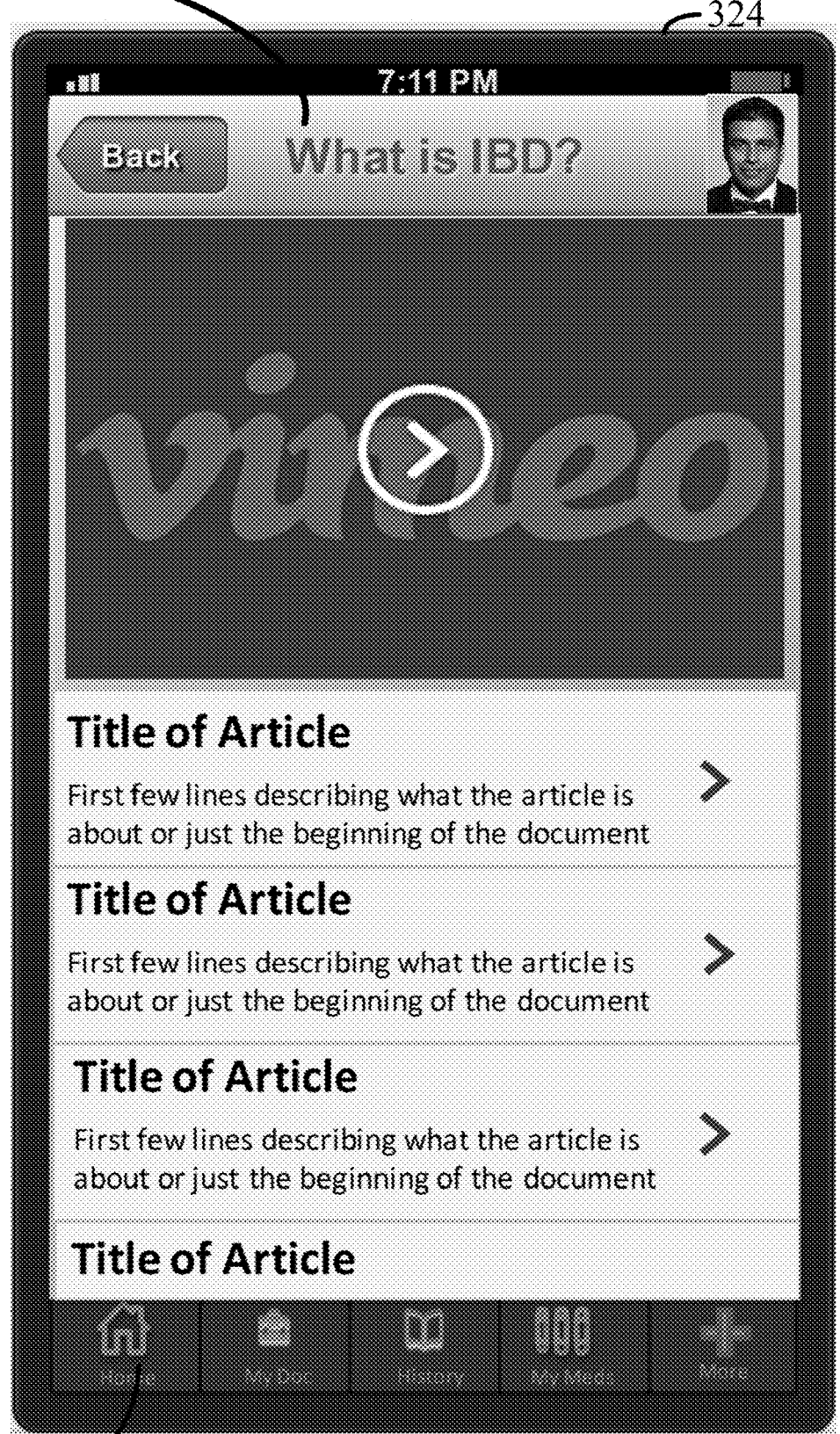
FIG. 25 illustrates another panel of a medical resource module within a gastrointestinal indication monitoring application in accordance with an aspect of the present disclosure.

Referring to FIGS. 3, 6 and 24, in some embodiments, the gastrointestinal indication monitoring module 426 includes a medical resource module 324 that comprises information regarding the chronic gastrointestinal indication. In some embodiments, the medical resource module 324 comprises a browser panel that provides options to the subject 216 for reviewing the information regarding the chronic gastrointestinal indication. For example, by selection of affordance 324 for the medical resource module 324 of FIG. 6, panel 2402 of FIG. 24 is displayed in some embodiments. Here, the subject may find out further information about their chronic gastrointestinal indication, such as what as the nature of the indication 2404, medications for the indication 2406, surgery options for the indication 2408, symptoms of the indication 2410, preventative care 2412, and current ongoing trials for the indication 2414. In turn, selecting affordance 2404 in panel 2402 leads to a corresponding panel 2502, in some embodiments, illustrated in FIG. 25, in which further information regarding the chronic gastrointestinal indication is provided. By selecting the home key 640, the subject is returned to panel 401 of FIG. 6.

In some embodiments, the gastrointestinal indication monitoring module 426 includes an alert module 326 that works with the alerts lookup table 226 of the chronic gastrointestinal indication tracking server 200 to provide alerts to the subject 216. In some embodiments, the alerts lookup table 226 comprises a plurality of alerts, where each alert comprises one or more corresponding trigger conditions in a plurality of trigger conditions and one or more actions in a plurality of actions. For example, in some embodiments, a quality of life score of the subject 216 is compared on a temporal basis with each trigger condition of each alert in the alerts lookup table and, when the quality of life score of the subject on the temporal basis matches a trigger condition of the alert module 326, issues a corresponding alert. In some embodiments this alert is communicated to the subject 216.

In some embodiments, the alert module 326 communicates fired alerts to chronic gastrointestinal indication tracking server 200 which, in turn, communicates the alerts to one or more devices 104 associated with subject caretakers. This further facilitates remote monitoring of patients. In varying embodiments, such communication is in the form of text messages, E-mail, or outbound calls generated by an interactive voice response (IVR) system.

Moreover, providers or health systems can delegate regular monitoring of patient data received by the disclosed systems and methods to personnel who can monitor patients closely and alert providers as needed. In some embodiments, referring to FIG. 4, a device 104 associated with a caretaker or medical practitioner of a subject 216, is a smart phone. In other embodiments, a device 104 is not a smart phone but rather is a tablet computer, desktop computer, emergency vehicle computer, or other form or wired or wireless networked device. In some embodiments, device 104 has any or all of the circuitry, hardware components, and software components found in the device 102 depicted in FIG. 3. In the interest of brevity and clarity, only a few of the possible components of device 104 are shown in order to better emphasize the additional software modules that are installed on device 104.

In typical embodiments, device 104 has one or more processing units (CPU's) 452, a network or other communications interface 470, a memory 457 (e.g., random access memory), a user interface 456, the user interface 456 including a display 458 and input 460 (e.g., keyboard, keypad, touch screen), an optional accelerometer 467, an optional GPS 469, one or more communication busses 462 for interconnecting the aforementioned components, and a power system 468 for powering the aforementioned components. In some embodiments, the input 460 is touch-sensitive display, such as a touch-sensitive surface. In some embodiments, the user interface 456 may include one or more soft keyboard embodiments. The soft keyboard embodiments may include standard (QWERTY) and/or non-standard configurations of symbols on the displayed icons.

Device 104 optionally includes, in addition to accelerometer(s) 417, a magnetometer (not shown) and a GPS 419 (or GLONASS or other global navigation system) receiver for obtaining information concerning the location and orientation (e.g., portrait or landscape) of device 104.

It should be appreciated that device 104 is only one example of a portable multifunction device, and that device 104 optionally has more or fewer components than shown in FIG. 4 (or in FIG. 3), optionally combines two or more components, or optionally has a different configuration or arrangement of the components. The various components shown in FIG. 4 are implemented in hardware, software, firmware, or a combination thereof, including one or more signal processing and/or application specific integrated circuits.

As illustrated in FIG. 4, a device 104 preferably comprises an operating system 472 that includes procedures for handling various basic system services. A device 104 further comprises an electronic address 474 (e.g., a mobile phone number, social media account, or e-mail address) associated with the caretaker that is used by the chronic gastrointestinal indication tracking server 200 to provide information pertaining to the caretaker. For example, in some embodiments, information in the subject data store 214 associated with a subject 216 the caretaker is responsible for (e.g., from questionnaires completed by the subject) is communicated to quality of life evaluation module 476 on the device 104 for evaluation by the caretaker. In such embodiments, the quality of life evaluation module 476 provides an overall quality of life score for the subject 216, over a period of time, based on such data. In some embodiments the communicated data includes a plurality of component quality of life scores, and each component quality of life score in the plurality of component quality of life scores is associated with at least one condition of a chronic gastrointestinal indication. In some embodiments, such a quality of life score is communicated in the absence of caregiver input directly on the chronic gastrointestinal indication tracking server and/or directly by the gastrointestinal indication monitoring application 426 on device 102.

Now that details of a system 48 for monitoring subjects with chronic gastrointestinal indications has been disclosed, details regarding a flow chart of processes and features of the system, in accordance with an embodiment of the present disclosure, are disclosed with reference to FIGS. 5A through 5F.

Block 502. While running an application (e.g.) gastrointestinal indication monitoring application 426 on an Internet-enabled electronic device (e.g., device 102 of FIG. 3), there is provided, on a repeating basis (e.g., daily, weekly, every two weeks, monthly) over a period of time (e.g., over the course of three weeks, a month, three months, half a year, a year, two years, five years), a questionnaire within the application regarding a plurality of conditions. In some embodiments, the questionnaire is provided on a recurring basis (e.g., between every two and ten days) (508). In some embodiments, the Internet-enabled electronic device is a tablet or smart phone (524).

Each condition in the plurality of conditions arises, at least in part, from a chronic gastrointestinal indication associated with a user. In some embodiments, the chronic gastrointestinal indication is inflammatory bowel disease (e.g., Crohn's disease, ulcerative colitis, or indeterminate colitis) (510). In some embodiments, the chronic gastrointestinal indication is obesity or irritable bowel syndrome (512). In some embodiments, the user has undergone a bariatric surgical procedure to alleviate the chronic gastrointestinal condition (e.g., a gastric bypass, a sleeve gastrectomy, insertion of an adjustable gastric band, or a biliopancreatic diversion with duodenal switch) (514). In some embodiments, the chronic gastrointestinal indication is gastrointestinal neoplasia (516). In some embodiments, the chronic gastrointestinal indication is Celiac disease (518). In some embodiments, the chronic gastrointestinal indication is a food allergy (e.g., allergy is to cow's milk, eggs, fish, peanuts, shell fish, soy, tree nuts, or wheat) (520). In some embodiments, the chronic gastrointestinal indication is a food intolerance (to lactose, sucrose, maltose, histamine, tyramine, salicylate, tartrazine, benzoates, monosodium glutamate, or a food dye) (522).

In some embodiments, the plurality of conditions comprises anxiety, fatigue, social discomfort, leisure, stress level, abdomen pain, depression, gas, weight maintenance, tension, bowel incident, and anger (504). In some embodiments, the plurality of conditions comprises two or more conditions selected from anxiety, fatigue, social discomfort, leisure, stress level, abdomen pain, depression, gas, weight maintenance, tension, bowel incident, and anger. (504).

In some embodiments the questionnaire comprises a series of questions regarding inflammatory bowel disease.

In some embodiments the questionnaire comprises the Short Inflammatory Bowel Disease Questionnaire—SIBDQ). See Irvine et al., 1996 "The Short Inflammatory Bowel Disease Questionnaire: a quality of life instrument for community physicians managing inflammatory bowel disease." CCRPT Investigators Canadian Crohn's Relapse Prevention Trial. Am J Gastroenterol. 1996 August; 91(8): 1571-1578, (PubMed: 8759664), which is hereby incorporated by reference. The SIBDQ questionnaire consists of ten questions scored in four domains: bowel symptoms, emotional health, systemic systems, and social function. FIG. 14, illustrates administration of the Short Inflammatory Bowel Disease Questionnaire. In FIG. 14, for each question 14, the user is provided with a slide bar 1460 in order to allow the user to select between a low value and a high value to indicate a degree to which the user presently associates with the corresponding condition.

In some embodiments, the questionnaire comprises questions regarding overall health.

In some embodiments the questionnaire comprises the General Quality of Life Questionnaire (EQ-5D), which is a standardized instrument for measuring generic quality of life. See de Charro, 2001, "EQ-5D: a measure of health status from the EuroQol Group." Ann Med. July; 33(5):337-43, (PubMed: 11491192), which is hereby incorporated by reference. Applicable to a wide range of health conditions and treatments, it provides a simple descriptive profile and a single index value for health status. EQ-5D is primarily designed for self-completion by respondents. It is cognitively simple and takes only a few minutes to complete. It is generally recognized that a change of 0.5 points (on a scale of 1-7) is the minimal clinically important difference (MCID), consistent with moderate effect size.

In some embodiments the questionnaire comprises eHEALS, which is an 8-item measure of eHealth literacy developed to measure consumers' combined knowledge, comfort, and perceived skills at finding, evaluating, and applying electronic health information to health problems. See Norman et al., 2006, "eHEALS: The eHealth Literacy Scale," J Med Internet Res. 8(4): e27, doi: 10.2196/jmir.8.4.e27. (PubMed: 17213046), which is hereby incorporated by reference in its entirety. This instrument has been psychometrically validated and its score positively correlated with intention to use personal health records.

In some embodiments, the questionnaire comprises the Patient Activation Measure (PAM-13, Hibbard et al., 2005, "Development and testing of a short form of the patient activation measure," Health Serv Res. 2005 December; 40 (6 Pt 1):1918-1930, hereby incorporated by reference in its entirety) to measure patient activation and engagement with health.

In some embodiments, eHEALS and PAM-13 are not provided on a repeating basis. In some embodiments, eHEALS and PAM-13 are not provided at all.

In some embodiments, the questionnaire includes questions regarding medications, adherence to medication, quality indicators, and questions regarding emergency visits.

In general, the questionnaire comprises a plurality of questions, and each respective question in the plurality of questions (i) is associated with a corresponding condition in the plurality of conditions and (ii) comprises an affordance (e.g., a slide bar, an input field, a plurality of radio buttons, a drop-down menu, etc.) that is configured to allow the user to select between a low value and a high value to indicate a degree to which the user presently associates with the corresponding condition. In some embodiments, the questionnaire further includes questions that are not directly associated with a condition in the plurality of conditions, such as number of emergency room visits.

In some embodiments, the low value is a numerical "1" indicating that the user does not associate with the corresponding condition and the high value is a numerical "10" indicating the user highly associates with the corresponding condition (506). More generally, in some embodiments, the low value is a first number indicating that the user does not associate with the corresponding condition and the high value is another number, other than the first number, indicating the user highly associates with the corresponding condition and the user can pick low number or the high number or any of a plurality of numbers that fall between the low number and the high number. In some embodiments, the low value is a first number indicating that the user associates with the corresponding condition and the high value is another number, other than the first number, indicating the user does not associate with the corresponding condition and the user can pick low number or the high number or any of a plurality of numbers that fall between the low number and the high number. Alternatively, as illustrated in FIGS. 14 and 15, the user pushes an annotated slide bar to a position that most closely associates with how the user presently relates to the subject condition (e.g. "none of the time,", "all of the time," "no problems," "some problems," "immobile," "unable," etc.). In some embodiments, the questionnaire input module 314 converts the slide bar positions into a number between the low number and the high number for the condition.

In some embodiments, the affordance provided to a user to answer a question in the questionnaire is a slide bar that is configured to be moved by the user to any one of a predetermined number of positions (e.g., 7 positions) between and inclusive of the low value and the high value to indicate a degree to which the user presently associates with the corresponding condition (526).

Referring to FIG. 15, in some embodiments, the plurality of questions in the questionnaire includes a mobility query (e.g. "I have some problems in walking about" 1504-1), a self-care query (1504-2), and an activity (work, study, housework, family or leisure) query (1504-3) (528).

Advantageously, usage of the application (e.g., gastrointestinal indication monitoring application) by the user reduces a propensity of the user to require live medical practitioner care (e.g., in the form of an outpatient doctor visit, ambulatory care, or emergency room visit) during the period of time by a threshold amount (e.g., is at least 10 percent, at least 20 percent, at least 30 percent, at least 40 percent, or at least fifty percent) (530). This is because most of the data is entered by patients (subjects). Thus, the cost of running the gastrointestinal indication monitoring application 426 is very low as compared to traditional disease registries, and more easily scaled and sustained.

Figure 5A:
Figure 5B:

Block 532. Referring to FIG. 5B, the responses to the questionnaire are stored in the questionnaire data store 328 (FIG. 3) associated with the user in the electronic device 102. Typically, such storage occurs each time the user responds to the questionnaire using the affordances associated with the plurality of questions of the questionnaire. In some embodiments, the responses to the questionnaire are stored in a questionnaire data store associated with the user that is addressable (e.g., across a network connection) by the electronic device 102 but this data store is not actually stored in the devices 102. For instance, in some such embodiments, the data store is stored in server 200. Typically, such storage occurs each time the user responds to the questionnaire using the affordances associated with the plurality of questions of the questionnaire.

Block 534. Referring to FIG. 5C, responsive to a report request from the user, a user report is provide comprising a graphical quality of life measure of the user as a function of time, within the application (e.g., the gastrointestinal indication monitoring application 426), based upon answers to the plurality of questions in the questionnaire over the period of time. FIG. 6 illustrates this. In FIG. 6, a graphical measure of QOL 310 is provided based on answers to QOL questionnaire questions and a separate graphical measure of symptoms 404 is provided. The graphical quality of life measure incorporates (i) a subjective assessment, made by the user, of a social factor affected by the chronic gastrointestinal indication and (ii) an objective assessment of an illness factor associated with the gastrointestinal indication (536). Examples of social factors include, but are not limited to, a mood of the user, an anxiety level of the user, a depression level of the user, an amount of pain incurred by the user, fatigue incurred by the user, pain incurred by the user, the amount of sports engaged by the user, and the amount of tension incurred by the user (548). Examples of illness factors include, but are not limited to, a number of bowel movements per day incurred by the user, abnormal white blood cell counts, abnormal haemoglobin count, abnormal erythrocyte sedimentation rate, abnormal plasma viscosity, abnormal neutrophil count, and weight. As illustrated in FIG. 6, the user report comprises a condition plot (e.g., QOL 310) as a function of time derived from the responses to the questionnaire.

In some embodiments, the graphical quality of life measure is interactive and includes instructions for providing the user an action plan based upon the graphical quality of life measure upon request of the user (544). In some embodiments, the graphical quality of life measure is color coded using a color schema, wherein each color in the color schema indicates a different quality of life tertile (546). For example, in some embodiments, a dark green value indicates the QOL value is in the best QOL tertile, a light green value indicates the QOL value is in the second best QOL tertile, a yellow value indicates the value QOL is in the second worst QOL tertile, and a red/orange value indicates the QOL value is in the worst QOL tertile.

Referring to FIG. 6, the user report illustrated comprises a checklist of care 602 indicating a number of care tasks associated with the chronic gastrointestinal indication the user has completed. Referring to FIG. 10, in some embodiments the checklist of care is provided in panel 1001 which details which of the interventions the subject has not accomplished 1002 and which interventions the subject has accomplished 1004. For instance, referring to FIG. 10, examples of interventions in the checklist of care include a vaccination 1004, a bone density test 1006, mucosal healing 1006 and an annual colonoscopy 1008. Moreover, the subject can search for interventions in the checklist of care using the search interface 1012. Selection of any of these interventions on panel 1001 leads to more information regarding an intervention in the checklist of care. For example, selection of vaccination 1004 of FIG. 10 leads to panel 1102 of FIG. 11 in which more information regarding vaccinations is provided.

Returning to FIG. 6, in some embodiments, the user report further comprises an indication of a number of hospital and emergency room visits 312 the user has participated in during a predetermined period of time (e.g., the past three months) (540). In typical embodiments this includes a visual representation 360 of resource utilization.

Block 550. Referring to FIG. 5D, information in the questionnaire data store 328 associated with the user from the questionnaire, obtained by the providing, is communicated to a remote device (e.g., chronic gastrointestinal indication tracking server 200) for evaluation by a medical practitioner. In some embodiments, the information is then stored as questionnaire response history 218 in the subject data store in the chronic gastrointestinal indication tracking server 200. In some embodiments, the information is formatted for computation of an overall quality of life score for the user, over the period of time, based on a plurality of component quality of life scores. Each component quality of life score in the plurality of component quality of life scores is associated with at least one condition in the plurality of conditions (552). The user report comprises a condition plot as a function of time derived from the responses to the questionnaire (e.g., QOL value 310 illustrated in FIG. 6).

Block 554. Referring to FIG. 5D, in some embodiments, the Internet-enabled electronic device 102 optionally further comprises, or has access to an alerts lookup table 226 comprising a plurality of alerts. In the system illustrates in FIGS. 1-3, this table 226 is illustrated as being resident in chronic gastrointestinal indication tracking server 200. However, in other embodiments, it is resident in device 102. Each alert 228 in table 226 comprises a corresponding trigger condition 230 in a plurality of trigger conditions and an action 232 in a plurality of actions. In some embodiments, an alert module 326 compares the quality of life score of the user on a temporal basis with each trigger condition 230 of each alert 228 in the alerts lookup table 226 and, when the quality of life score of the user on the temporal basis matches a trigger condition 230 of a first alert 228 in the plurality of alerts, the corresponding action 232 of the first alert 228 is fired (556). In one example of this, the trigger condition 230 for the first alert 228 is a drop in the quality of life score by a predetermined amount over a predetermined amount of time, and the first alert 232 is a notification to the user, through the gastrointestinal indication monitoring application 426, for follow up care or appointment scheduling with a medical practitioner (558). In some embodiments, firing of the first alert 228 comprises initiating a visual alert, an audible alert or a vibrational alert.

As an example of an alert, in some embodiments, patient symptom scores may identify patients with a change in the severity of their disease that will be associated with a red-yellow-green color indication of how they are doing. In such embodiments, this will trigger a pop-up or emailed alert to contact their provider and discuss the change in symptoms. As another example of an alert, automated alerts to providers will be triggered for patients "not doing well" on the basis of their health assessments, providing opportunities for intervention such as recommending an office visit sooner than scheduled.

Block 560. Referring to FIG. 5E, in some embodiments, a psychosocial intervention request is received and, responsive to receiving the psychosocial intervention request, a psychosocial interaction activity is provided to the user within the gastrointestinal indication monitoring application 426 (562). In some embodiments, the psychosocial interaction activity comprises instructions on how to self-administer an injectable, a relaxation technique, instructions on sleep hygiene, instructions for performing an exercise to manage fatigue, or instructions on anger control (564). In some embodiments, the psychosocial interaction activity comprises instructions (e.g., a picture, a document, or a uniform resource location link to a document) on how to self-administer an injectable, a relaxation technique, instructions on sleep hygiene, instructions for performing an exercise to manage fatigue, or instructions on anger control.

In some embodiments, the gastrointestinal indication monitoring application 426 optionally further comprises a medication module 316 that tracks one or more medicines that the user is taking to alleviate the chronic gastrointestinal indication (566). For instance, in some embodiments, selecting affordance 316 of panel 401 of FIG. 6 leads to panel 1602 of FIG. 16 which provides ways for the subject to track medications the subject 216 is taking to alleviate the chronic gastrointestinal indication. For instance, affordance 1604 enables the subject to add new medications, affordance 1606 allows the subject to peruse current medications, and affordance 1608 allows the subject to review past medications taken for the chronic gastrointestinal indication.

In some embodiments, the gastrointestinal indication monitoring application 426 optionally further comprises an allergy module 318 that tracks one or more allergies associated with the user (568). For instance, selecting affordance 318 of panel 401 of FIG. 6 leads to panel 2002 of FIG. 20, in some embodiments, which provides ways for the subject to indication which medications 2004 to which the subject has allergies. In turn, selecting a medication 2004 in panel 2002 leads to a corresponding panel 2102 in some embodiments, illustrated in FIG. 21, in which further information regarding the allergy is provided, such as the date first noticed 2104, and the symptoms that arose 2106.

In some embodiments, the gastrointestinal indication monitoring application 426 optionally further includes a resource use module 312 that tracks utilization of the user of one or more resources (570). In some such embodiments, the resource use module 312 comprises an input mechanism for inputting usage by the user of resources in the one or more resources, and a plotting mechanism for plotting usage of the one or more resources by the user over a period of time (572). In some embodiments, the one or more resources is a plurality of resources and the plurality of resources comprises emergency room visits and hospitalization visits. FIGS. 7 through 9, described above, illustrate different examples of resource use module 312.

In some embodiments, the gastrointestinal indication monitoring application 426 optionally further includes a medications/medication history module 316 that tracks the use of medications by the user. In some such embodiments, the medications/medication history module 316 comprises an input mechanism for inputting medication types and medication usage by the user. For instance, in some embodiments, selecting affordance 316 of panel 401 of FIG. 6 leads to panel 1602 of FIG. 16 which provides ways for the subject to track medications the subject 216 is taking to alleviate the chronic gastrointestinal indication. For instance, affordance 1604 enables the subject to add new medications, affordance 1606 allows the subject to peruse current medications, and affordance 1608 allows the subject to review past medications taken for the chronic gastrointestinal indication.

In some embodiments, the gastrointestinal indication monitoring application 426 optionally further includes an allergy module 318 that tracks the allergies of the user. In some such embodiments, the allergies module 318 comprises an input mechanism for inputting allergies by the user. For instance, selecting affordance 318 of panel 401 of FIG. 6 leads to panel 2002 of FIG. 20, in some embodiments, which provides ways for the subject to indication which medications 2004 to which the subject has allergies. In turn, selecting a medication 2004 in panel 2002 leads to a corresponding panel 2102 in some embodiments, illustrated in FIG. 21, in which further information regarding the allergy is provided, such as the date first noticed 2104, and the symptoms that arose 2106.

In some embodiments, the gastrointestinal indication monitoring application 426 optionally further includes a medical practitioner caretaker module 320 that tracks contact information for medical practitioner caretakers associated with the user (578). In some such embodiments, the medical practitioner caretaker module 320 comprises an input mechanism for inputting medical practitioner caretaker information by the user. For example, by selection of the affordance 320 for the medical practitioner caretaker module 320 of FIG. 6, panel 2202 of FIG. 22 is displayed in some embodiments. Here, the subject is provided with affordances for their primary physician 2204, gastroenterologist 2206, and pharmacy 2208. Further, the subject is provided with affordances for adding new notes 2210 or reviewing past notes from prior doctor visits 2212.

In some embodiments, the gastrointestinal indication monitoring application 426 further includes a pharmacy module 322 that tracks contact information for one or more pharmacies associated with the user (580). In some such embodiments, the pharmacy module 322 comprises an input mechanism for inputting pharmacy information by the user. For example, by selection of the affordance 322 for the medical practitioner caretaker module 322 of FIG. 6, panel 2302 of FIG. 23 is displayed in some embodiments. Here, the subject is provided with affordances for entering pharmacy information, such as address 2304, and phone number 2306, and prescriptions 2308. By selecting the home key 640, the subject is returned to panel 401 of FIG. 6.

In some embodiments, the gastrointestinal indication monitoring application 426 further includes a medical resource module 324 that comprises information regarding the chronic gastrointestinal indication. In some such embodiments, the medical resource module 324 comprises a browser panel that provides options to the user for reviewing the information regarding the chronic gastrointestinal indication. For example, by selection of affordance 324 for the medical resource module 324 of FIG. 6, panel 2402 of FIG. 24 is displayed in some embodiments. Here the subject may find out further information about their chronic gastrointestinal indication, such as what as the nature of the indication 2404, medications for the indication 2406, surgery options for the indication 2408, symptoms of the indication 2410, preventative care 2412, and current ongoing trials for the indication 2414. In turn, selecting affordance 2404 in panel 2402 leads to a corresponding panel 2502 in some embodiments, illustrated in FIG. 25, in which further information regarding the chronic gastrointestinal indication is provided.

Example 1—Approach for Inflammatory Bowel Disease

In inflammatory bowel disease (IBD), optimal approaches to management vary for patients with different phenotypes and extent of disease and past surgical history. Hence, a single quality metric cannot define a heterogeneous disease such as IBD, unlike hypertension and diabetes. Furthermore, IBD affects patients not only physically, but also in social, professional and emotional domains. Overall well-being of IBD patients cannot be achieved if these dimensions are not improved. Unfortunately, most of the currently proposed QI initiatives in IBD are process measures, and do not include QOL or clinically meaningful outcomes such as clinical remission or hospitalizations, that matter most to patients and their state of health.

In this example, a more comprehensive assessment is provided by complementing the traditional quality metrics with measures of the patient's quality of life (QOL). Here, QOL is defined as "a global measure of patient's perceptions, illness experience, and functional status that incorporates social, cultural, psychological, and disease-related factors." QOL is used to inform outcomes in clinical encounters, monitor population health, and as end points in clinical trials. NIH Patient Reported Outcomes Measurement Information System (nihpromis.org) and more recently Project Health Design (projecthealthdesign.org) have provided valuable insights into generic measurements for QOL. In this example, the feasibility of capturing QOL during routine office encounters to assess overall quality in patients with IBD is detailed. The inclusion of disease phenotype and surgical history details allows for the risk-adjustment of the data and allows comparisons across different patient groups.

In this example, the burden of measuring quality is advantageously decreased by allowing patients to play a proactive role. Measuring even limited quality of care metrics carry a prohibitively high administrative and cost burden. The estimated costs from the Institute for Healthcare Improvement QI initiative for either congestive heart failure or diabetes ranged from $81,000 to $148,000 per organization. See Cretin et al., 2004, "An evaluation of collaborative interventions to improve chronic illness care. Framework and study design," Eval Rev. February: 28 (1): 28-51, doi:10.1177/0193841X03256298 (PubMed: 14750290), which is hereby incorporated by reference in its entirety. Reported costs for inpatient QI for a hospital have ranged from $2 million to $21 million, with the majority of the costs attributed to collecting and reporting quality metrics for national organizations. See Chen et al., 2009, "Costs of quality improvement: a survey of four acute care hospitals," Jt Comm J Qual Patient Saf., 35(11):544-550, which is hereby incorporated by reference. This burden of measuring quality is likely to increase exponentially when multiple quality of care metrics are included in quality measurement. In the present disclosure, a patient-centric mobile health (mhealth) strategy for measuring and improving care is adopted. Quality and outcomes is directly measured from patients through Internet-enabled devices (including Smart Phones and Tablet computers), thus decreasing the administrative burden and cost of Quality Improvement efforts.

Figure 33:
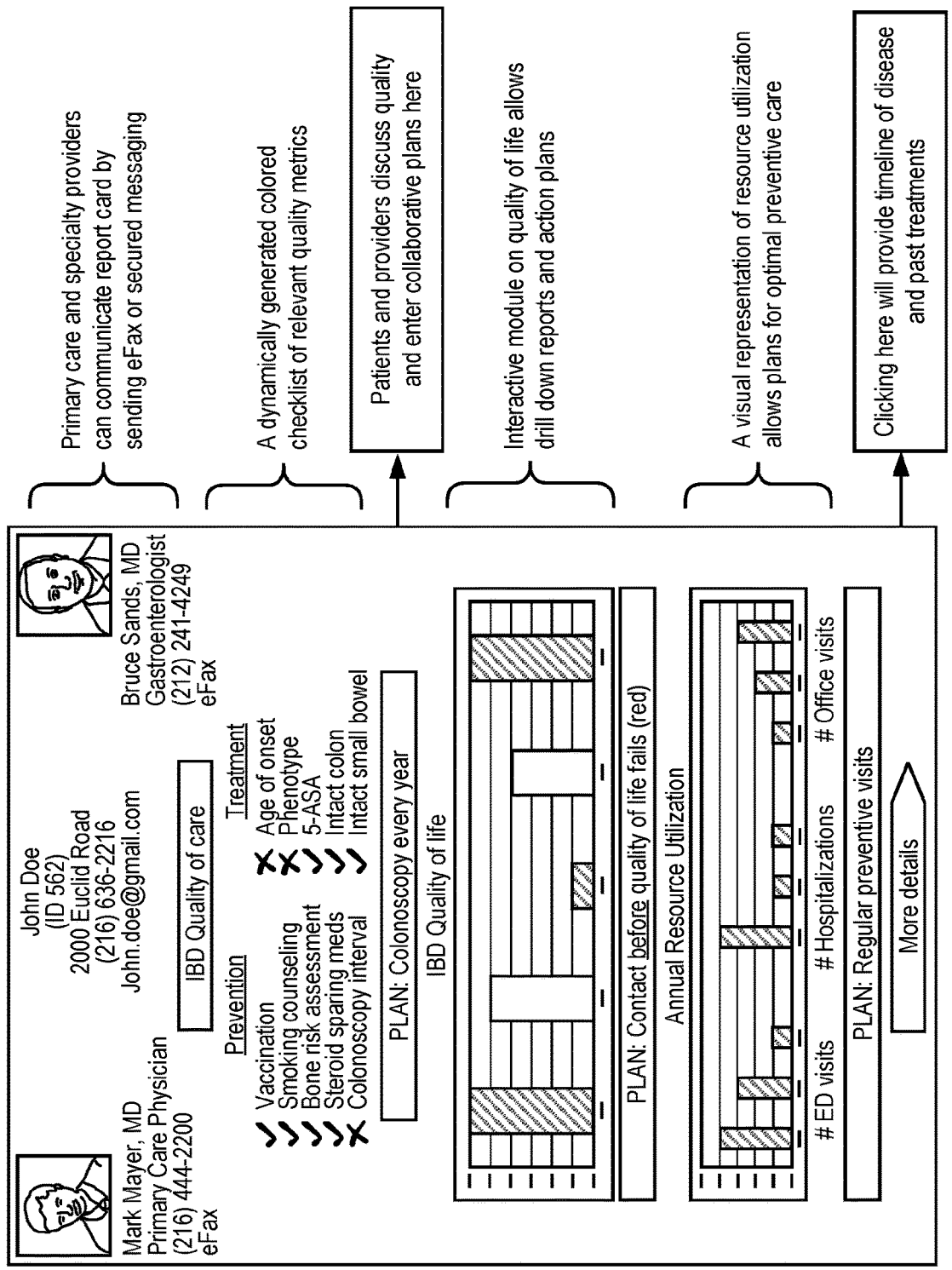
FIG. 33 illustrates a screenshot of a proposed interactive Quality Report Card that allows for an update of quality metrics, quality of life and resource utilization from Internet-enabled devices and provider electronic health records in accordance with an aspect of the present disclosure.

Improving the effectiveness of Quality Improvement initiatives by allowing decisions at the point of care as opposed to after-the-fact. Currently, there is no well accepted national model for Quality Improvement. Most of the Quality Improvement projects to date involve some kind of data abstraction from the clinical encounters that is fed into a registry to allow benchmarking, risk adjustment and quality reporting. This cycle takes anywhere from a few weeks to a few months and happens long after the patient has left the health care facility. Patients are not involved in measuring or improving quality. Thus, an important patient-physician "productive interaction" opportunity to improve outcomes at the point of care is missed. See Wagner et al., 1998, "Chronic disease management: what will it take to improve care for chronic illness?" Eff Clin Pract. 1 (1): 2-4, which is hereby incorporated herein by reference. In the present disclosure, patients and practitioners are provided with electronic Quality Report Cards at the point of care that incorporates the checklist approach. This allows them to bring discussion about quality and outcomes to office encounters and meaningfully engage in collaborative decision making, rather than attempting to comply with indicators afterwards. FIG. 33 illustrates a screenshot of such a proposed interactive Quality Report Card that allows for an update of quality metrics, QOL and resource utilization from Internet-enabled devices and provider electronic health records in accordance with an aspect of the present disclosure.

The present example seeks to define a set of comprehensive quality indicators for IBD patients based on the hypothesis that patients and providers have different, often complementary, views on evaluating and improving health care quality. For this, proposed quality of care indicators for IBD patients from national societies and published literature will be drawn upon, including AGA Digestive Health Outcome Registry and Physician Quality Reporting Initiative measures; and CCFA process and outcome metrics.

Focus groups of patients and semi-structured interviews of physicians will be conducted to (i) identify metrics that may not have been addressed such as mucosal healing, quality of life, concomitant depression, fatigue, etc., (ii) determine which metrics can be accurately captured by patients and which will require physician documentation (such as mucosal healing and phenotype) and, (iii) elicit feedback on pilot interfaces, and its decision support (Quality Report Card, alerts and dashboard reports), and (iv) query underserved populations in an attempt to explore and address sociodemographic and language barriers to adoption.

Another aim of this example is to improve the design of the gastrointestinal indication monitoring application 426 and measure comprehensive quality indicators. The hypothesis behind this aim is that many quality metrics can be captured directly from patients, thus decreasing the burden and cost of QI. Remaining metrics can be documented by physicians if QI platform is integrated with electronic health records. To further this aim, better end-user experience with the development of "native" android and iPad IBDPROMISE applications (app) that will generate electronic Quality Report Card in physician offices and at home will be made. Better visualization of QOL that will allow subject to meaningfully interpret their QOL scores (e.g. utilizing green, yellow and red to represent good, fair and poor QOL tertiles) will be made. A visual "time series chart" that allows a snapshot from past to present of patients' entire IBD history including past surgeries, medications and QOL will be implemented. A "bowel damage score" will also be implemented. Further, the gastrointestinal indication monitoring application 426 will be integrated with enterprise electronic health records to allow documentation of physician reported quality metrics into the gastrointestinal indication monitoring application 426 consistent with checklist QI rules. Further, self-management principles (including links to CCFA health education content at ibdetermined.org with support from P30 Center of Excellence in Self-Management Research (SMART Center, Case Western Reserve University), will be implemented.

Another aim of this example is to conduct a randomized controlled trial to determine the impact of the gastrointestinal indication monitoring application 426 in improving outcomes (quality of care, QOL, patient adherence, disease control and resource utilization). The hypothesis behind this aim is that a patient-centric self-monitoring and collaborative decision support platform will lead to sustainable improvement in overall quality of IBD patients. The patient population will be drawn from those needing longitudinal care and that consent to participate to be followed for a period of two years. Inclusion criteria are (1) Age ≥18 years, (2) internet or Smartphone access and (3) ability to complete a web-based questionnaire in English language. Exclusion criteria are (1) presence of short bowel syndrome, stoma or pouch, (2) disabling perianal disease or (3) presence of a condition or disease that, in the opinion of the investigators, may make it exceedingly difficult for the patient to use the gastrointestinal indication monitoring application 426, including, but not limited to, advanced dementia. Since the primary outcome is improvement in quality of care metrics, which are applicable to patients with any disease activity, patients with mild disease activity will not be excluded.

All consecutive IBD patients presenting to IBD center will be assessed for eligibility and provided Tablet computers in waiting room. Patients, who provide informed consent, will be enrolled and followed before randomization. Randomization: After baseline measurement and follow-up of at least 6 months, patients will be randomized into the gastrointestinal indication monitoring application 426 arm and control using computer generated random number generator (18 months intervention). This will allow allocation concealment and prevent selection bias from treating physician. The period before randomization will allow optimization of office workflow and baseline measurement of quality and its trend in the two arms.

Patients randomized to the gastrointestinal indication monitoring application 426 arm will be asked to update quality metrics, SIBDQ and questions about hospitalizations or emergency visits during office visits and every month. A five-point drop in SIBDQ will alert both the patient and treating physician about the need for close follow-up and/or appointment scheduling. In addition, dashboard access will be provided to physicians to see detailed monthly quality reports of their patient panel in the gastrointestinal indication monitoring application 426 arm. During a visit to the treating provider, patients in the gastrointestinal indication monitoring application 426 arm will be able to update their information and print-out their Quality Report Card (detailing their disease summary, quality metrics and a graph showing the trend of SIBDQ scores and resource utilization over time, FIG. 1). Providers will utilize the Quality Report card for collaborative decision making and QI interventions at the point of care. Quality metrics will be categorized as met or unmet. Only eligible quality metrics will be considered for Quality Report Card and analysis (e.g. a patient with end ileostomy will not be eligible for colonoscopy surveillance metric). Patients in the control arm will enter data at baseline, during office visits and at the end of the study, but will not receive any decision support (Quality Report Card, alert or dashboard views).

Study instruments. A combination of different questionnaires (e.g., the Short Inflammatory Bowel Disease Questionnaire—SIBDQ), symptom updates, and quality indicators relevant for evaluating patient status will be the data collected during this study through the gastrointestinal indication monitoring application 426 (e.g., FIGS. 14 and 15). The Short Inflammatory Bowel Disease Questionnaire is a validated and reliable tool to measure health-related QOL in adult patients with IBD. See Irvine et al., 1996 "The Short Inflammatory Bowel Disease Questionnaire: a quality of life instrument for community physicians managing inflammatory bowel disease." CCRPT Investigators Canadian Crohn's Relapse Prevention Trial. Am J Gastroenterol. 1996 August; 91(8):1571-1578, (PubMed: 8759664), which is hereby incorporated by reference. The questionnaire consists of ten questions scored in four domains: bowel symptoms, emotional health, systemic systems, and social function. The SIBDQ is a respected QOL questionnaire used extensively in academic research and clinical trials. Study patients in the control arm and interventional arm will complete an SIBDQ as part of a survey to objectively measure QOL at baseline and at exit (52 weeks or 104 weeks). Additionally, patients in the intervention arm will be asked to complete the SIBDQ every 2 weeks; this will be used to classify patients as having "good control," "fair control," or "poor control."

General Quality of Life Questionnaire. EQ-5D is a standardized instrument for measuring generic QOL. See de Charro, 2001, "EQ-5D: a measure of health status from the EuroQol Group." Ann Med. July; 33 (5): 337-43, (PubMed: 11491192), which is hereby incorporated by reference. Applicable to a wide range of health conditions and treatments, it provides a simple descriptive profile and a single index value for health status. EQ-5D is primarily designed for self-completion by respondents. It is cognitively simple and takes only a few minutes to complete. It is generally recognized that a change of 0.5 points (on a scale of 1-7) is the minimal clinically important difference (MCID), consistent with moderate effect size. Patients in the intervention arm will be asked to complete the EQ-5D every 2 weeks.

eHEALS is an 8-item measure of eHealth literacy developed to measure consumers' combined knowledge, comfort, and perceived skills at finding, evaluating, and applying electronic health information to health problems. See Norman et al., 2006, "eHEALS: The eHealth Literacy Scale," J Med Internet Res. 8(4): e27, doi: 10.2196/jmir.8.4.e27. (PubMed: 17213046), which is hereby incorporated by reference in its entirety. This instrument has been psychometrically validated and its score positively correlated with intention to use personal health records. Patient Activation Measure (PAM-13, Hibbard et al., 2005, "Development and testing of a short form of the patient activation measure," Health Serv Res. 2005 December; 40 (6 Pt 1):1918-1930, hereby incorporated by reference in its entirety) will be used to measure patient activation and engagement with health. eHEALS and PAM-13 will be completed by patients in both arms during entry and exit surveys only. Quality indicators are included from a list of indicators published by national societies and finalized through a Delphi panel of IBD providers. See Allen et al., 2014 website "Adult inflammatory bowel disease physician performance measures set" gastro.org/practice/qualityinitiatives/IBD Measures.pdf, and website "The physician quality reporting system," American Gastroenterology Association gastro.org/practice/quality-initiatives/cms-physician-qualitative-report-initiative, each of which is hereby incorporated by reference. This is updated on a recurring basis by either providers or patients, along with hospitalization and emergency department visit information.

Primary analysis will be a comparison of the proportion of patients in each group (the gastrointestinal indication monitoring application 426 vs. control) who meet all eligible quality metrics at week 104. A secondary analysis will compare proportion of patients in disease control at week 104 (SIBDQ >53, approximating IBDQ remission score >170), proportion of patients highly adherent to medications, percentage-point improvement in quality metrics from baseline to week 104 aggregated for each arm and improvement in disease-specific and generic QOL score from baseline. In addition, a determination of predictors (clinical, sociodemographic and ehealth literacy) of meeting quality metrics will be made. Exploratory analysis. Starting in year two, pilot projects exploring integration of laboratory markers (such as fecal Calprotectin) and endoscopic disease severity (such as mucosal healing) with the gastrointestinal indication monitoring application 426 to improve prediction of disease severity and generate data for future research endeavors will be made.

REFERENCES CITED AND ALTERNATIVE EMBODIMENTS

All references cited herein are incorporated herein by reference in their entirety and for all purposes to the same extent as if each individual publication or patent or patent application was specifically and individually indicated to be incorporated by reference in its entirety for all purposes.

The present invention can be implemented as a computer program product that comprises a computer program mechanism embedded in a nontransitory computer readable storage medium. For instance, the computer program product could contain the program modules shown in any combination of FIG. 1, 2, 3, or 4. These program modules can be stored on a CD-ROM, DVD, magnetic disk storage product, or any other non-transitory computer readable data or program storage product.

Many modifications and variations of this invention can be made without departing from its spirit and scope, as will be apparent to those skilled in the art. The specific embodiments described herein are offered by way of example only. The embodiments were chosen and described in order to best explain the principles of the invention and its practical applications, to thereby enable others skilled in the art to best utilize the invention and various embodiments with various modifications as are suited to the particular use contemplated. The invention is to be limited only by the terms of the appended claims, along with the full scope of equivalents to which such claims are entitled.

What is claimed is:

1. A method, comprising:
   at a first Internet-enabled electronic device with a display:
      while running an application on the first Internet-enabled electronic device:
         providing, on a repeating basis over a period of time, a questionnaire within the application regarding a plurality of conditions, wherein each condition in the plurality of conditions arises, at least in part, from a chronic gastrointestinal indication associated with a user, wherein the questionnaire comprises a plurality of questions, and each respective question in the plurality of questions (i) is associated with a corresponding condition in the plurality of conditions and (ii) comprises an affordance that is configured to allow the user to select between a low value and a high value to indicate a degree to which the user presently associates with the corresponding condition;
         storing responses to the questionnaire in a data store associated with the user in the first Internet-enabled electronic device each time the user responds to the questionnaire using the affordances associated with the plurality of questions of the questionnaire;
         responsive to a report request from the user, providing an interactive user report comprising a respective single scalar value representing a quality of life measure of the user at each respective time point in a plurality of time points across a period of time, within the application, based upon answers to the plurality of questions in the questionnaire at each respective time point in the plurality of time points, wherein each respective single scalar value representing a quality of life measure incorporates (i) a subjective assessment, made by the user, of a social factor affected by the chronic gastrointestinal indication at the respective time point, wherein the social factor is a mood of the user, an anxiety level of the user, a depression level of the user, an amount of pain incurred by the user, fatigue incurred by the user, an amount of sports engaged by the user, or an amount of tension incurred by the user and (ii) an objective assessment of an illness factor associated with the gastrointestinal indication at the respective time point, wherein the illness factor is a number of bowel movements per day incurred by the user, a white blood cell count of the user, a hemoglobin count of the user, an erythrocyte sedimentation rate of the user, a plasma viscosity of the user, a neutrophil count of the user, or a weight of the user;
         communicating the interactive user report comprising information in the data store associated with the user from the questionnaire, obtained by the providing, to a remote, second Internet-enabled electronic device for evaluation by a medical practitioner;
         comparing, at each respective time point in the plurality of time points, the respective single scalar value representing a quality of life measure of the user with a respective trigger condition for each respective alert in an alerts lookup table, wherein the alerts lookup table is stored in the first Internet-enabled electronic device and comprises a plurality of alerts, each respective alert in the plurality of alerts comprising a corresponding trigger condition in a plurality of trigger conditions and a corresponding action in a plurality of actions, wherein the trigger condition for the first alert is a drop in the quality of life measure by a predetermined amount over a predetermined amount of time; and,
            when the respective single scalar value representing a quality of life measure of the user matches a respective trigger condition for a first alert in the plurality of alerts, firing the corresponding action of the first alert, wherein the corresponding action of the first alert is a notification to the user, through the application, for follow up care or appointment scheduling with a medical practitioner and wherein firing of the corresponding action of the first alert comprises initiating a visual alert, an audible alert or a vibrational alert;
      inputting a date of each user emergency room visit for the chronic gastrointestinal indication associated with the user and a date of each hospitalization visit by the user for the chronic gastrointestinal indication associated with the user occurring during the period of time through an input mechanism of a resource use module of the application run on the first Internet-enabled electronic device; and
      plotting, through a plot mechanism of the resource use module of the application run on the first Internet-enabled electronic device, a number of emergency room visits and a number of hospitalization visits made by the user, for the chronic gastrointestinal indication associated with the user, during the period of time,
      wherein the number of hospitalization visits is plotted separately from the number of emergency room visits in the period of time.

2. The method of claim 1, the method further comprising:
   receiving a psychosocial intervention request from the remote device; and
   responsive to receiving the psychosocial intervention request, providing a psychosocial interaction activity to the user within the application.

3. The method of claim 1, wherein the plurality of conditions comprises anxiety, fatigue, social discomfort, leisure, stress level, abdomen pain, depression, gas, weight maintenance, tension, bowel incident, and anger.

4. The method of claim 1, wherein the low value is a numerical 1 indicating that the user does not associate with the corresponding condition and the high value is a numerical 10 indicating the user highly associates with the corresponding condition.

5. The method of claim 1, wherein the providing the questionnaire is done on a recurring basis.

6. The method of claim 1, wherein the user report further comprises a condition plot as a function of time derived from the responses to the questionnaire.

7. The method of claim 1, wherein the user report further comprises a checklist of care indicating a number of care tasks associated with the chronic gastrointestinal indication the user has completed and wherein the user report further comprises an indication of a number of hospital and emergency room visits the user has participated in during a predetermined period of time.

8. The method of claim 1, wherein the chronic gastrointestinal indication is inflammatory bowel disease, obesity, irritable bowel syndrome, gastrointestinal neoplasia, Celiac disease, a food allergy, or a food intolerance.

9. The method of claim 1, wherein the user has undergone a bariatric surgical procedure to alleviate the chronic gastrointestinal condition wherein the bariatric surgical procedure is selected from the group consisting of a gastric bypass, a sleeve gastrectomy, an insertion of an adjustable gastric band, or a biliopancreatic diversion with duodenal switch.

10. The method of claim 1, wherein the user report further comprises a visual representation of resource utilization.

11. The method of claim 1, wherein the user report comprising the respective single scalar value representing the quality of life measure is interactive and includes instructions for providing the user an action plan based upon the quality of life measure upon request of the user.

12. The method of claim 1, wherein the respective single scalar value representing the quality of life measure of the user at each respective time point is color coded using a color schema, wherein each color in the color schema indicates a different quality of life tertile.

13. The method of claim 1, wherein the affordance of a question in the plurality of questions is a slide bar that is configured to be moved by the user to any one of a predetermined number of positions between and inclusive of the low value and the high value to indicate a degree to which the user presently associates with the corresponding condition.

14. The method of claim 1, wherein the social factor comprises a mood of the user, an anxiety level of the user, a depression level of the user, an amount of pain incurred by the user, or fatigue incurred by the user and wherein the illness factor comprises a number of bowel movements per day incurred by the user.

15. The method of claim 1, wherein the plurality of questions in the questionnaire includes a mobility query, a self-care query, and an activity query.

16. The method of claim 1, wherein the application further comprises a medication module that tracks one or more medicines that the user is taking to alleviate the chronic gastrointestinal indication.

17. The method of claim 1, wherein the application further includes a medications/medication history module that tracks the use of medications by the user, the medications/medication history module comprising:
an input mechanism for inputting medication types and medication usage by the user.

18. The method of claim 1, wherein the application further includes a medical practitioner caretaker module that tracks contact information for medical practitioner caretakers associated with the user, the medical practitioner caretaker module comprising:
an input mechanism for inputting medical practitioner caretaker information by the user.

19. The method of claim 1, wherein the application further includes a pharmacy module that tracks contact information for one or more pharmacies associated with the user, the pharmacy module comprising:
an input mechanism for inputting pharmacy information by the user.

20. A non-transitory computer readable storage medium for monitoring a chronic gastrointestinal indication, wherein the non-transitory computer readable storage medium stores instructions, which when executed by a first Internet-enabled device, cause the first Internet-enabled device to:
provide, on a repeating basis over a period of time, a questionnaire within an application regarding a plurality of conditions, wherein each condition in the plurality of conditions arises, at least in part, from the chronic gastrointestinal indication, wherein the questionnaire comprises a plurality of questions, and each respective question in the plurality of questions (i) is associated with a corresponding condition in the plurality of conditions and (ii) comprises an affordance that is configured to allow the user to select between a low value and a high value to indicate a degree to which the user presently associates with the corresponding condition;
store responses to the questionnaire in a data store associated with the user each time the user responds to the questionnaire using the affordances associated with the plurality of questions of the questionnaire;
responsive to a report request from the user, provide an interactive user report comprising a respective single scalar value representing a quality of life measure of the user at each respective time point in a plurality of time points across a period of time based upon answers to the plurality of questions in the questionnaire at each respective time point in the plurality of time points, wherein each respective single scalar value representing a quality of life measure incorporates (i) a subjective assessment, made by the user, of a social factor affected by the chronic gastrointestinal indication at the respective time point, wherein the social factor is a mood of the user, an anxiety level of the user, a depression level of the user, an amount of pain incurred by the user, fatigue incurred by the user, an amount of sports engaged by the user, or an amount of tension incurred by the user and (ii) an objective assessment of an illness factor associated with the gastrointestinal indication at the respective time point, wherein the illness factor is a number of bowel movements per day incurred by the user, a white blood cell count of the user, a hemoglobin count of the user, an erythrocyte sedimentation rate of the user, a plasma viscosity of the user, a neutrophil count of the user, or a weight of the user;
communicate the interactive user report comprising information in the data store associated with the user from the questionnaire, obtained by the providing, to a remote, second Internet-enabled device other than the first device, for evaluation by a medical practitioner;
compare, at each respective time point in the plurality of time points, the respective single scalar value representing a quality of life measure of the user with a respective trigger condition for each respective alert in an alerts lookup table, wherein the alerts lookup table is stored in the first Internet-enabled device and comprises a plurality of alerts, each respective alert in the plurality of alerts comprising a corresponding trigger condition in a plurality of trigger conditions and a corresponding action in a plurality of actions wherein the trigger condition for the first alert is a drop in the quality of life measure by a predetermined amount over a predetermined amount of time; and, when the respective single scalar value representing a quality of life measure of the user matches a respective trigger condition for a first alert in the plurality of alerts, firing the corresponding action of the first alert, wherein the corresponding action of the first alert is a notification to the user, through the application, for follow up care or appointment scheduling with a medical practitioner and wherein firing of the corresponding action of the first alert comprises initiating a visual alert, an audible alert or a vibrational alert;

inputting a date of each user emergency room visit for the chronic gastrointestinal indication associated with the user and a date of each hospitalization visit by the user for the chronic gastrointestinal indication associated with the user occurring during the period of time through an input mechanism of a resource use module of the application run on the first Internet-enabled electronic device;

plotting, through a plot mechanism of the resource use module of the application run on the first Internet-enabled electronic device, a number of emergency room visits and a number of hospitalization visits made by the user, for the chronic gastrointestinal indication associated with the user, during the period of time, wherein the number of hospitalization visits is plotted separately from the number of emergency room visits in the period of time.

21. An Internet-enabled computer system, comprising:
one or more processors;
memory; and
one or more programs stored in the memory for execution by the one or more processors, the one or more programs comprising instructions for:

providing, on a repeating basis over a period of time, a questionnaire regarding a plurality of conditions, wherein each condition in the plurality of conditions arises, at least in part, from a chronic gastrointestinal indication associated with a user, wherein the questionnaire comprises a plurality of questions, and each respective question in the plurality of questions (i) is associated with a corresponding condition in the plurality of conditions and (ii) comprises an affordance that is configured to allow the user to select between a low value and a high value to indicate a degree to which the user presently associates with the corresponding condition;

storing responses to the questionnaire in a data store associated with the user each time the user responds to the questionnaire using the affordances associated with the plurality of questions of the questionnaire;

responsive to a report request from the user, providing an interactive user report comprising a respective single scalar value representing a quality of life measure of the user at each respective time point in a plurality of time points across a period of time based upon answers to the plurality of questions in the questionnaire at each respective time point in the plurality of time points, wherein each respective single scalar value representing a quality of life measure incorporates (i) a subjective assessment, made by the user, of a social factor affected by the chronic gastrointestinal indication at the respective time point, wherein the social factor is a mood of the user, an anxiety level of the user, a depression level of the user, an amount of pain incurred by the user, fatigue incurred by the user, an amount of sports engaged by the user, or an amount of tension incurred by the user and (ii) an objective assessment of an illness factor associated with the gastrointestinal indication at the respective time point, wherein the illness factor is a number of bowel movements per day incurred by the user, a white blood cell count of the user, a hemoglobin count of the user, an erythrocyte sedimentation rate of the user, a plasma viscosity of the user, a neutrophil count of the user, or a weight of the user;

communicating the interactive user report comprising information in the data store associated with the user from the questionnaire, obtained by the providing, to a remote Internet-enabled device, for evaluation by a medical practitioner;

comparing, at each respective time point in the plurality of time points, the respective single scalar value representing a quality of life measure of the user with a respective trigger condition for each respective alert in an alerts lookup table, wherein the alerts lookup table is stored in the Internet-enabled computing system and comprises a plurality of alerts, each respective alert in the plurality of alerts comprising a corresponding trigger condition in a plurality of trigger conditions and a corresponding action in a plurality of actions, wherein the trigger condition for the first alert is a drop in the quality of life measure by a predetermined amount over a predetermined amount of time; and, when the respective single scalar value representing a quality of life measure of the user matches a respective trigger condition for a first alert in the plurality of alerts, firing the corresponding action of the first alert, wherein the corresponding action of the first alert is a notification to the user, through the application, for follow up care or appointment scheduling with a medical practitioner and wherein firing of the corresponding action of the first alert comprises initiating a visual alert, an audible alert or a vibrational alert;

inputting a date of each user emergency room visit for the chronic gastrointestinal indication associated with the user and a date of each hospitalization visit by the user for the chronic gastrointestinal indication associated with the user occurring during the period of time through an input mechanism of a resource use module of the application run on the first Internet-enabled electronic device;

plotting, through a plot mechanism of the resource use module of the application run on the first Internet-enabled electronic device, a number of emergency room visits and a number of hospitalization visits made by the user, for the chronic gastrointestinal indication associated with the user, during the period of time, wherein the number of hospitalization visits is plotted separately from the number of emergency room visits in the period of time.

* * * * *

UNITED STATES PATENT AND TRADEMARK OFFICE
CERTIFICATE OF CORRECTION

| | | |
|---|---|---|
| PATENT NO. | : 11,791,020 B2 | Page 1 of 1 |
| APPLICATION NO. | : 15/999470 | |
| DATED | : October 17, 2023 | |
| INVENTOR(S) | : Ashish Atreja et al. | |

It is certified that error appears in the above-identified patent and that said Letters Patent is hereby corrected as shown below:

In the Specification

In Column 1, beginning at Line 22, please amend the paragraph below the STATEMENT REGARDING FEDERALLY SPONSORED RESEARCH OR DEVELOPMENT from:
Part of the work performed during development of this invention utilized U.S. Government funds through grant number K23 DK097451 of the National Institute of Health (NIH). The U.S. Government has certain rights in the invention.
To:
This Invention was made with government support under Grant No. DK097451 awarded by the National Institutes of Health. The government has certain rights in the invention.

Signed and Sealed this
Twenty-seventh Day of August, 2024

Katherine Kelly Vidal
*Director of the United States Patent and Trademark Office*